United States Patent
Shishido et al.

(10) Patent No.: US 6,236,057 B1
(45) Date of Patent: May 22, 2001

(54) METHOD OF INSPECTING PATTERN AND APPARATUS THEREOF WITH A DIFFERENTIAL BRIGHTNESS IMAGE DETECTION

(75) Inventors: Chie Shishido; Takashi Hiroi, both of Yokohama; Haruo Yoda, Nishitama-gun; Masahiro Watanabe, Yokohama; Asahiro Kuni, Setagaya-ku; Maki Tanaka, Yokohama; Takanori Ninomiya, Hiratsuka; Hideaki Doi, Oota-ku; Shunji Maeda, Yokohama; Mari Nozoe, Oume; Hiroyuki Shinoda, Choufu; Atsuko Takafuji, Nerima-ku; Aritoshi Sugimoto, Bunkyou-ku; Yasutsugu Usami, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/610,954

(22) Filed: Jul. 6, 2000

Related U.S. Application Data

(63) Continuation of application No. 09/081,636, filed on May 20, 1998, now Pat. No. 6,087,673.

(30) Foreign Application Priority Data

May 21, 1997 (JP) .................................................. 9-131460

(51) Int. Cl.$^7$ .................................................. G01N 21/88
(52) U.S. Cl. .................................... 250/559.45; 250/208.1
(58) Field of Search ........................... 250/559.45, 559.4, 250/559.46, 310, 306, 208.1; 356/237.4, 235.5; 382/149, 145

(56) References Cited

U.S. PATENT DOCUMENTS

| 4,996,434 | * | 2/1991 | Tanaka | 250/492.3 |
| 5,663,569 | | 9/1997 | Hayano | 250/559.45 |

FOREIGN PATENT DOCUMENTS

| 57-196377 | 2/1982 | (JP) . |
| 3-177040 | 1/1991 | (JP) . |

* cited by examiner

*Primary Examiner*—Que T. Le
(74) *Attorney, Agent, or Firm*—Antonelli, Terry, Stout & Kraus, LLP

(57) ABSTRACT

A method and apparatus for inspecting a pattern, a first image of a first area on a sample is acquired by imaging the first area formed as a first pattern, and the first image is memorized. A second image of a second area on the sample is acquired by imaging the second area formed as a second pattern which is to be the same as the first pattern. A defect of the first pattern is detected by acquiring a differential image between the first image and the second image. The detection of the defect includes processing the differential image by using information of brightness corresponding to both of the first image and the second image.

23 Claims, 11 Drawing Sheets

DETECTION IMAGE f1 (x, y)

COMPARISON IMAGE g1 (x, y)

METHOD OF INSPECTING PATTERN AND APPARATUS THEREOF WITH A DIFFERENTIAL BRIGHTNESS IMAGE DETECTION

CROSS REFERENCE TO RELATED APPLICATION

This is a continuation of U.S. application Ser. No. 09/081,636, filed May 20, 1998, now U.S. Pat. No. 6,087,673, the subject matter of which is incorporated by reference herein.

BACKGROUND OF THE INVENTION

The present invention relates to a method of inspecting a pattern and an apparatus thereof, in which a defect or a candidate for a defect is inspected by obtaining an image indicating physical properties of objects such as a semiconductor wafer, a TFT, and a photo mask with the use of an electron beam or a light beam, and by then comparing the image with an image obtained differently. More particularly, the present invention relates to a method of inspecting a pattern and an apparatus thereof, in which a microscopic defect or a candidate for a microscopic defect is inspected.

Concerning an inspection for recognizing a defect of a pattern, known as a prior art technology 1, as disclosed in Japanese Laid-Open Patent Publication No. 57-196377, is as follows. First, a pattern of an object to be inspected, such as a semiconductor including a pattern with a repetition, is detected, and the pattern detected is stored. Then, position alignment is performed in a pixel or picture element unit between the detected pattern and a pattern stored in advance. Finally, a defect is recognized by extracting a mismatch between the two patterns over which the position alignment has been made. Also, known as a prior art technology 2, as disclosed in Japanese Laid-Open Patent Publication No. 3-177040, is a technique which makes it possible to improve, of a problem of a mismatch between the both images in a normal part, a portion of the problem that is attributed to a missing of a position at which the both images are to be detected. Namely, described in the prior art technology 2 is the following technique. First, a pattern of an object is detected as an image signal. Then, position alignment is performed in a pixel unit between the image signal of the detected pattern and an image signal of the pattern stored in advance or an image signal of the pattern detected differently. Still then, with one pixel or less of accuracy, additional position alignment is further made between the image signals over which the position alignment has been made in the pixel unit. Finally, a defect of the pattern is recognized by extracting and comparing errors of the image signals of the two patterns over which the additional position alignment has been made with one pixel or less of accuracy.

Between the two images to be compared, even in the normal part, there exists differences such as an infinitesimal difference in pattern configuration, a difference in a gradation or tone value, a distortion of the pattern, and a shift of the position, which are attributed to the object to be inspected and an image detecting system. Namely, the mismatch in the normal part is classified into a mismatch due to the object to be inspected and a mismatch due to the image detecting system. The mismatch due to the object to be inspected is caused by a subtle difference in repetition patterns produced through a wafer manufacturing process such as an exposure, a developing and an etching. This, on the detected images, appears as the infinitesimal difference in pattern configuration and the difference in the gradation value. The mismatch due to the image detecting system is caused by variations in illuminating light quantity, an oscillation of a stage, a variety of electrical noises, and a missing of the position at which the both images are to be detected. These, on the detected images, appear as a difference in a gradation value of partial images, the distortion of the pattern, and the position shift of the images.

In the above-mentioned prior art technology 1, there existed the following problem. Since the above-described factors cause the mismatch to occur even in the normal part, if every mismatched portion is judged to be a defect, it turns out that there occurs a lot of false information. If, in order to prevent this, a criterion for the defect judgement is lowered, it becomes impossible to detect a microscopic defect.

Also, in the above-mentioned prior art technology 2, of the infinitesimal difference in the pattern configuration, the difference in the gradation value, the distortion of the pattern, and the position shift, which are attributed to the object to be inspected and the image detecting system, there existed an effect of reducing an influence of the position shift between the images. The other differences, however, were not taken into consideration.

SUMMARY OF THE INVENTION

It is an object of the present invention to provide, in order to solve the above-mentioned problems accompanied by the prior arts, a method of inspecting a pattern and an apparatus thereof, which make it possible to further reduce the number of false information caused by a mismatch due to an object to be inspected and an image detecting system, and to detect a more microscopic defect or a candidate for a more microscopic defect.

It is another object of the present invention to provide, when a pattern formed on an object to be inspected is inspected by means of an electron microscope, a method of inspecting the pattern and an apparatus thereof, which make it possible to further reduce the number of false information caused by a mismatch due to the object to be inspected and an image detecting system, and to detect a more microscopic defect or a candidate for a more microscopic defect.

It is still another object of the present invention to provide a method of inspecting a pattern and an apparatus thereof, which make it possible to obtain an image signal having a stable gradation value (a value of light and shade) from an inspection through an electron microscope of a pattern formed on an object to be inspected, and to stably detect a more microscopic defect or a candidate for a more microscopic defect.

In order to attain the above-described object, the present invention is characterized by the configuration described below, when a defect or a candidate for a defect of an object to be inspected is detected by comparing a first two-dimensional image, on each pixel of which a gradation value is a sampling value of a physical quantity at each point in one area to be inspected on the object to be inspected, with a second two-dimensional image, on each pixel of which a gradation value is a sampling value at each point in the other area which is supposed to have the same physical quantity as the above-mentioned physical quantity.

Namely, the present invention is characterized by comprising the steps of performing position alignment between the first two-dimensional image and the second two-dimensional image in a pixel unit, calculating one pixel or less of position shift quantity of corresponding portions between the first two-dimensional image $f1(x, y)$ and the second two-dimensional image $g1(x, y)$ over which the position alignment has been made in the pixel unit, determining for each pixel sub(x, y), i.e. a distance (difference) between a partial image (an image in a smaller area) in the first two-dimensional image and a partial image (an image in a smaller area) in the second two-dimensional image which have the one pixel or less of position shift quantity, determining for each pixel an allowable range (threshold values thH(x, y) and thL(x, y) at an upper limit and a lower limit, respectively) of the distance (difference) from the one pixel or less of position shift quantity determined and gradation values of the first two-dimensional image and the second two-dimensional image, checking whether or not the above-described distance (difference) between the partial images falls within the above-described allowable range for each pixel, and judging a pixel, on which the distance between the partial images is within the allowable range, to be an non-defective candidate and a pixel, on which the distance between the partial images is beyond the allowable range, to be a defective candidate.

Also, the present invention is characterized by comprising the steps of performing position alignment between the first two-dimensional image and the second two-dimensional image in a pixel unit, calculating one pixel or less of position shift quantity of corresponding portions between the first two-dimensional image and the second two-dimensional image over which the position alignment has been made in the above-mentioned pixel unit, determining a distance (difference) between the first two-dimensional image and the second two-dimensional image in each of a plurality of states in which the position relationship between the first two-dimensional image and the second two-dimensional image is shifted in a variety of directions by predetermined quantities determined by α·β from a state in which the above-stated one pixel or less of position shift quantity has been amended, comparing with each other a distance (difference) between partial images in the both two-dimensional images determined for each of the above-mentioned position relationships in the plurality of states and determining for each pixel a maximum and a minimum of the distances between the partial images, determining for each pixel an allowable value (threshold values at an upper limit and a lower limit) of the distances between the partial images from a gradation value of the first two-dimensional image and that of the second two-dimensional image over which the position alignment has been made in the pixel unit, comparing a value obtained by adding the allowable value to the maximum with a value obtained by subtracting the allowable value from the minimum, and judging a pixel, on which the signs of them are opposite (the polarity is different), to be an non-defective candidate and a pixel, on which the signs of them are same (the polarity is same), to be a defective candidate.

Besides, the present invention provides a method and an apparatus for inspecting a defect or a candidate for a defect of an object to be inspected, by comparing a first two-dimensional image, on each pixel of which detected as a gradation value is a sampling value of a physical quantity at each point on the object to be inspected, with a second two-dimensional image on each pixel of which represented as a gradation value is a sampling value. Incidentally, in this invention, the second two-dimensional image is employed as an object compared with the first two-dimensional image. In addition, the present invention is characterized in that an allowable range is calculated in correspondence with a position shift quantity between an image in a predetermined area in the first two-dimensional image and an image in a predetermined area in the second two-dimensional image, a distance or a difference between the above-mentioned first two-dimensional image and the above-mentioned second two-dimensional image is determined using the gradation values, and a pixel is judged to be the defect or the candidate for the defect depending on whether or not the distance or the difference determined using the gradation values is within the calculated allowable range described above.

In addition, in the above-described method of inspecting a pattern and the apparatus thereof, the present invention is characterized by calculating a local change rate of a gradation value, using any one of the following formulas 14-1, 14-2, and 14-3, or enlarging the formulas 14-1, 14-2, and 14-3 up to n*n pixel in proximity to a pixel to which attention is being given. Assuming that f (x, y) is a gradation value of the pixel to which attention is being paid, and d x(x, y) and d y(x, y) are local change rates of the gradation value in a x-direction and a y-direction, respectively, the formulas to be used are as follows.

$$dx(x,y)=f(x+1,y)-f(x,y)$$

$$dy(x,y)=f(x,y+1)-f(x,y) \quad 14\text{-}1$$

$$dx(x,y)=[\{f(x+1,y)+f(x+1,y+1)\}-\{f(x,y)+f(x,y+1)\}]/2$$

$$dy(x,y)=[\{f(x,y+1)+f(x+1,y+1)\}-\{f(x,y)+f(x+1,y)\}]/2 \quad 14\text{-}2$$

$$dx(x,y)=dy(x,y)=\max\{f(x,y), f(x+1,y), f(x,y+1), f(x+1,y+1)\}-\min\{f(x,y), f(x+1,y), f(x,y+1), f(x+1,y+1)\} \quad 14\text{-}3$$

Moreover, in the above-described method of inspecting a pattern and the apparatus thereof, the present invention provides a method of calculating a variation allowable range of the gradation value, which is to be determined as a function of the local change rate of the gradation value, with the use of either of the following formulas 15-1, 15-2.

an upper limit in a variation allowable range of a gradation value at a coordinate $$(x,y)=|dx(x,y)*\alpha|+|dy(x,y)*\beta| \quad 15\text{-}1$$

a lower limit in a variation allowable range of a gradation value at a coordinate $$(x,y)=-|dx(x,y)*\alpha|-|dy(x,y)*\beta|$$

an upper limit in a variation allowable range of a gradation value at a coordinate $$(x,y)=\sqrt{\{(dx(x,y)*\alpha)^2+(dy(x,y)*\beta)^2\}} \quad 15\text{-}2$$

a lower limit in a variation allowable range of a gradation value at a coordinate $$(x,y)=-\sqrt{\{(dx(x,y)*\alpha)^2+(dy(x,y)*\beta)^2\}}$$

, assuming that dx(x,y) and dy(x,y) are the local change rates of the gradation value in a x-direction and a y-direction, respectively, which are calculated from gradation values of a plurality of pixels in proximity to the pixel to which attention is being paid, and α,β are real numbers greater than zero.

Furthermore, in the above-described method of inspecting a pattern and the apparatus thereof, the present invention provides a method of treating, in such a manner as to be described in any one of the following methods 16-1, 16-2, and 16-3, the variation allowable range of the gradation value which is to be determined as a function of a representative gradation value. 16-1 Employed as the representative gradation value is a maximum of the gradation value within a range of ρ*ρ pixel in proximity to a pixel (x, y) to which attention is being given, and the variation allowable range is determined as a function of the representative gradation value. 16-2 Employed as the representative gradation value is an average value of the gradation value within a range of ρ*ρ pixel in proximity to a pixel (x, y) to which attention is being given, and the variation allowable range is determined as a function of the representative gradation value. 16-3 A look-up table for the representative gradation value is prepared beforehand, and, in accordance therewith, the variation allowable range is determined.

Further, in the above-described method of inspecting a pattern and the apparatus thereof, the present invention is characterized in that a method of superposing values obtained by a plurality of methods out of the above-described methods (1), (2), and (3) is as follows. Summing up a plurality of values obtained by a plurality of methods out of the methods (1), (2), and (3), taking the square root of summation of squares of a plurality of values out of the methods (1), (2), and (3), or taking the square root of summation of a square of summation of a plurality of values out of the methods (1), (2), and (3), and a square of summation of the other plurality of values.

Still further, in the above-described method of inspecting a pattern and the apparatus thereof, the present invention is characterized by performing part of the whole process or the whole process with a plurality of pixels as one pixel.

Even further, in the above-described method of inspecting a pattern and the apparatus thereof, the present invention is characterized by embodying content described with a plurality of pixels as one pixel.

DESCRIPTION OF THE PREFERRED EMBODIMENTS

Described below, using the accompanying drawings, are embodiments of a method of inspecting a pattern and an apparatus thereof in connection with the present invention.

First Embodiment

Figure 1:
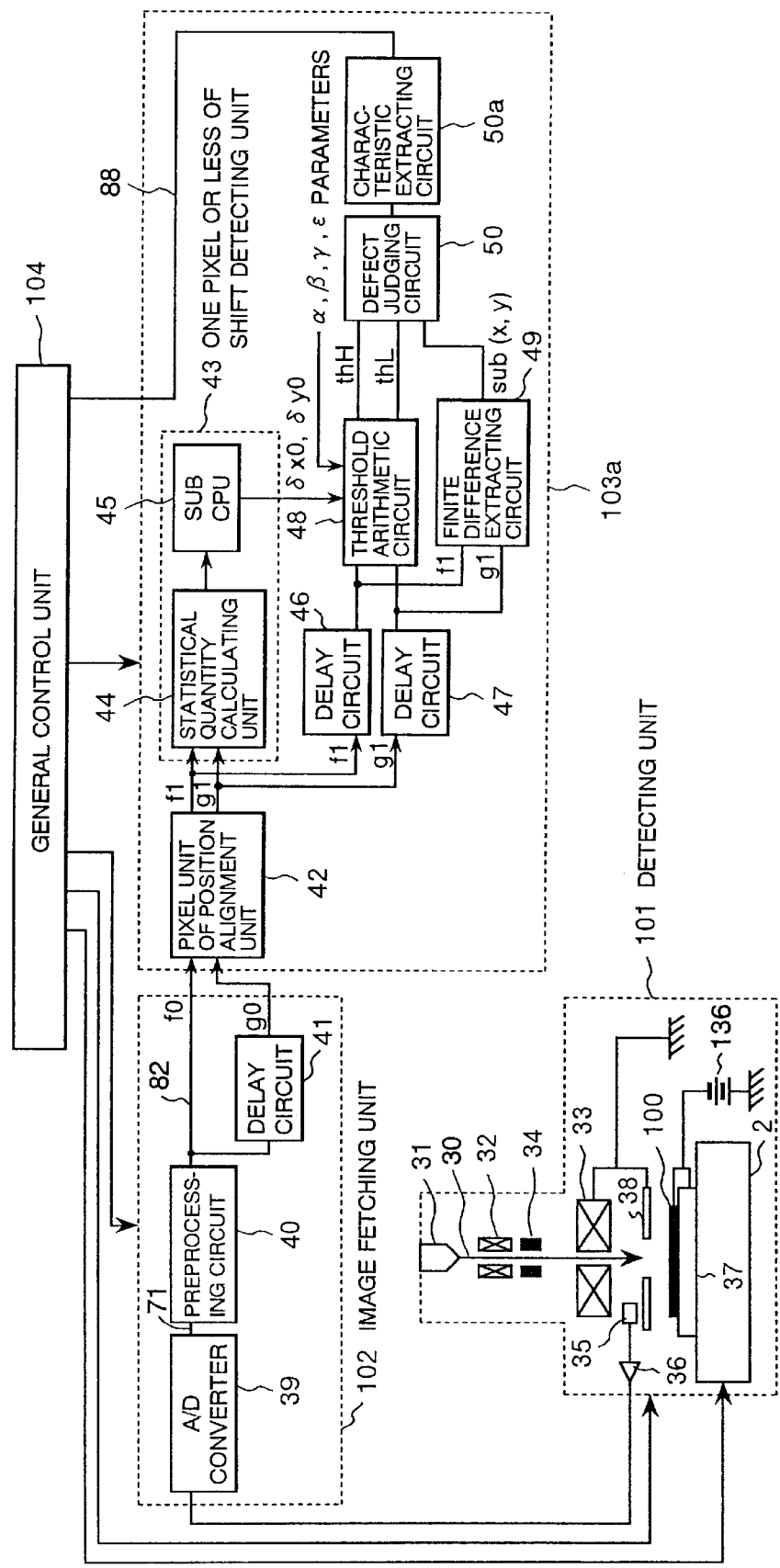
FIG. 1 is a schematic configuration diagram showing a first embodiment of a method of inspecting a pattern and an apparatus thereof in which an electron microscope in connection with the present invention is employed.

Shown in FIG. 1 is a first embodiment of a method of inspecting a pattern and an apparatus thereof in connection with the present invention. Here, irradiation of an electron beam 30 scans an object to be inspected 100 such as a wafer, thus detecting electrons produced from the object to be inspected 100. Then, based on variations in the intensity, an electron beam image of the scanned part is obtained so as to perform a patter inspection using the electron beam image.

Figure 2:
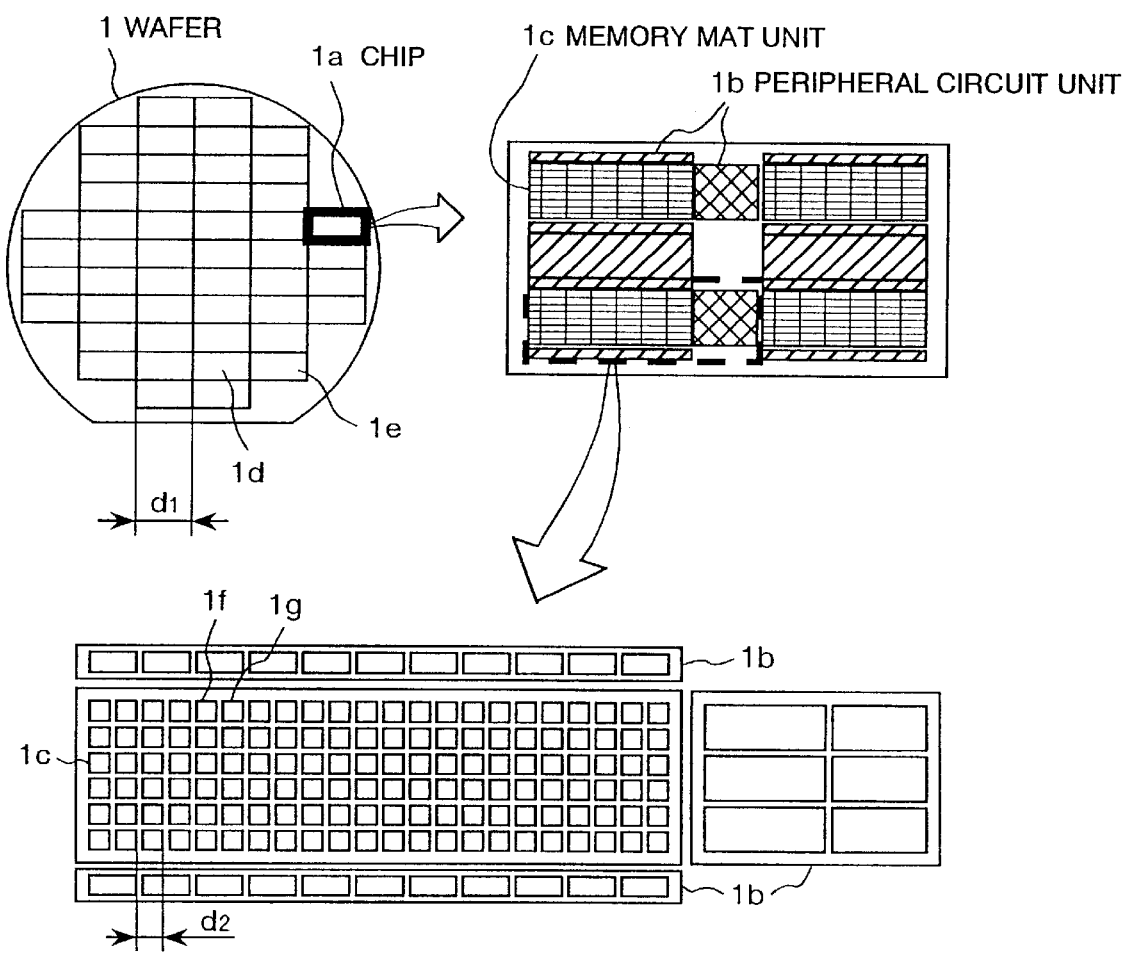
FIG. 2 is a layout diagram of a semiconductor wafer shown as an example of an object to be inspected in connection with the present invention.

Employed as the object to be inspected 100 is, for example, a semiconductor wafer 1 as shown in FIG. 2. Arranged on the semiconductor wafer 1 are a great umber of chips 1a, which finally turn out to become an identical product to each other. As is shown in an enlarged view of the Figure, pattern layout within a chip 1a comprises a memory mat unit 1c, on which memory cells are regularly arranged two-dimensionally at an identical pitch, and a peripheral circuit unit 1b. When applied to an inspection of a pattern in the semiconductor wafer 1, a defect is recognized by first storing a detection image on a chip (for example, a chip 1d) and then comparing it with a detection image on another chip (for example, a chip 1e) (hereinafter, referred to as "chip comparison"), or by first storing a detection image in a memory cell (for example, a memory cell 1f) and then comparing it with a detection image in another memory cell (for example, a memory cell 1g) (hereinafter, referred to as "cell comparison").

If repetition patterns on the object to be inspected 100 (taking the semiconductor wafer as an example, chips among themselves or cells among themselves) were strictly identical to each other and the same detection images were able to be obtained, recognition of a defect would be possible since only the defect mismatches when the images are compared with each other.

Actually, however, there does exist a mismatch between the both images even in a normal part. The mismatch in the normal part is classified into a mismatch due to an object to be inspected and a mismatch due to an image detecting system. The mismatch due to the object to be inspected is caused by a subtle difference in repetition patterns produced through a wafer manufacturing process such as an exposure, a developing and an etching. This, on the detected images, appears as an infinitesimal difference in the pattern configuration and a difference in a gradation value. The mismatch due to the image detecting system is caused by variations in illuminating light quantity, an oscillation of a stage, a variety of electrical noises, and a missing of the position at which the both images are to be detected. These, on the detected images, appear as a difference in a gradation value of partial images, distortion of the pattern, and position shift of the images.

In the first embodiment in connection with the present invention, a defect judgment is made in the following manner. First, a detection image (a first two-dimensional image), over which position alignment has been made in a pixel unit and the gradation value of which is f1(x,y) at a coordinate (x,y), is compared with a detection image (a second two-dimensional image), over which position alignment has been made in a pixel unit and the gradation value of which is g1(x,y) at a coordinate (x,y). Then, threshold values (allowable values), which are used at the time of judging a defect, are set for each pixel by considering a result of the comparison and such factors as position shift of the pattern and a difference in the gradation values. Finally, based on the threshold values (allowable values) set for each pixel, the defect judgment is made.

Figure 11:
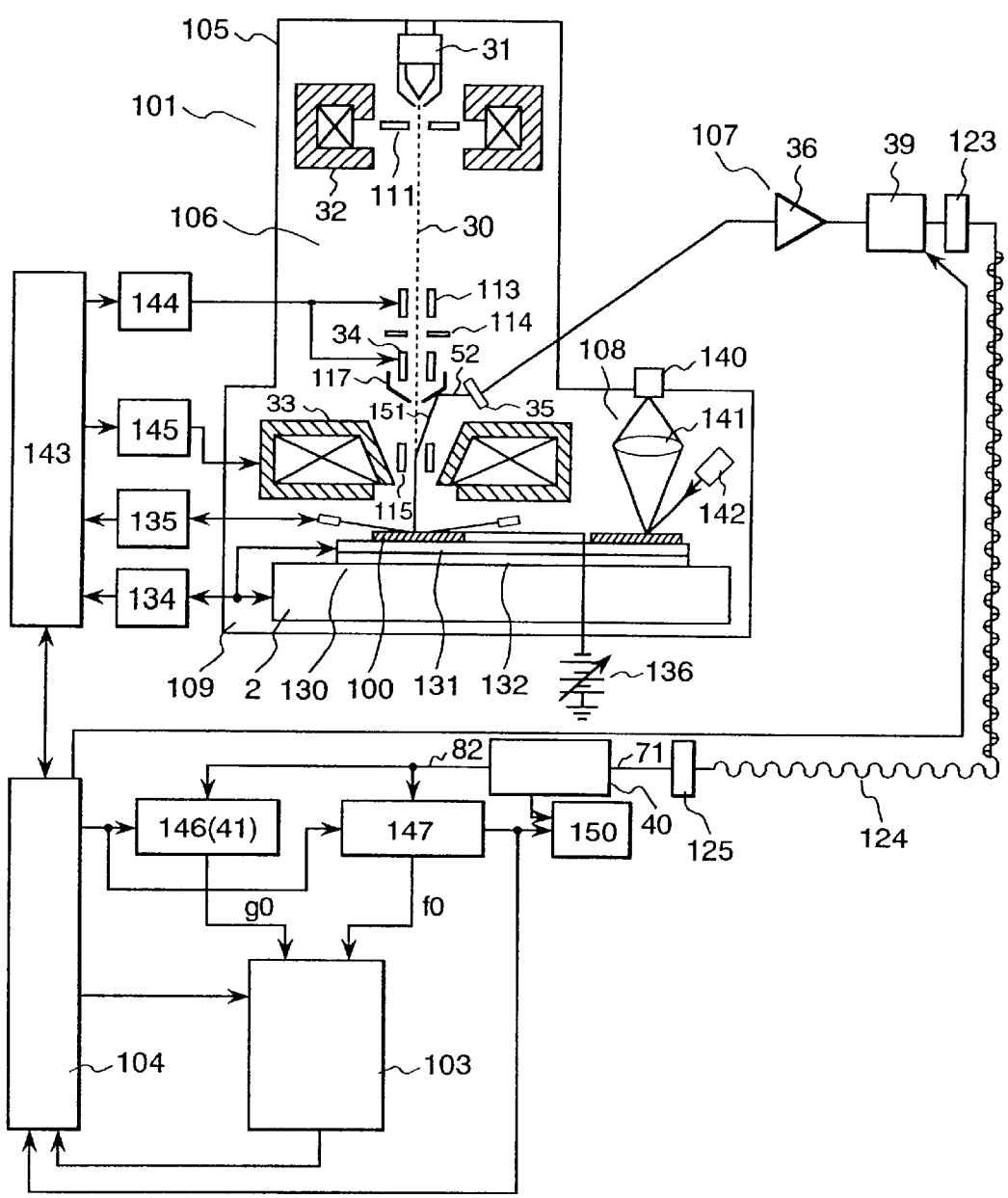
FIG. 11 is a schematic configuration diagram showing an embodiment of an electron microscope in connection with the present invention.

The present pattern inspecting system, as shown in FIG. 1 and FIG. 11, comprises a detecting unit 101, an image fetching unit 102, an image processing unit 103, and a general control unit 104 for controlling the whole system. Additionally, the present pattern inspecting system further comprises an inspection room 105 the inside of which is exhausted into a vacuum and a preliminary room (not illustrated) through which the object to be inspected 100 is transported into or out of the inspection room 105. The preliminary room is configured to be exhausted into a vacuum independently of the inspection room 105.

First, the description will be given below concerning the detecting unit 101, using FIG. 1 and FIG. 11. The inspection room 105 in the detecting unit 101 mainly comprises an electronic optical system 106, an electron detecting unit 107, a sample room 109, and an optical microscope unit 108. The electronic optical system 106 comprises an electron gun 31, an electron beam extraction electrode 111, a condenser lens 32, a blanking deflector 113, a scanning deflector 34, a diaphragm 114, an objective lens 33, a reflector 117, an EXB deflector 115, and a Faraday cup (not illustrated) for detecting a beam electric current. The reflector 117 is made conical in shape so as to have an effect of multiplexing secondary electrons.

Of units furnished in the electron detecting unit 107, for example, an electron detector 35, which detects electrons such as secondary electrons and reflected electrons, is provided above, for example, the objective lens 33 within the inspection room 105. An output signal of the electron detector 35 is amplified by an amplifier 36 provided outside the inspection room 105.

The sample room 109 comprises a sample stand 130, a X stage 131, a Y stage 132, a position monitoring range finder 134, and an inspected substrate height finder 135. Incidentally, the stages may be provided with a rotating stage.

The position monitoring range finder 134 monitors positions of units such as the stages 131 and 132, then transferring the result to the general control unit 104. Also, the general control unit 104 controls driving systems of the stages 131 and 132. This eventually makes it possible for the general control unit 104 to accurately grasp an area or a position onto which the electron beam 30 is irradiated based on these data.

The inspected substrate height finder 135 measures height of the object to be inspected 100 placed on the stages 131 and 132, using an optical measuring apparatus. Based on measurement data measured by the inspected substrate height finder 135, a focal length of the objective lens 33 for narrowing the electron beam 30 is dynamically amended so that the electron beam can be irradiated under a condition that the focus is always achieved on an area to be inspected. Incidentally, although, in FIG. 11, the height finder 135 is provided inside the inspection room 105, it is allowable that the height finder 135 is provided outside the inspection room 105 so as to introduce light into the inside of the inspection room 105 through the glass windows.

The optical microscope unit 108 and the electronic optical system 106 inside the inspection room 105 are in proximity to each other, and at the same time are located apart to such an extent that the both exerts no influence on each other. Naturally, the distance between the electronic optical system 106 and the optical microscope unit 108 is configured to be a known value. Moreover, the X stage 131 or the Y stage 132 is configured to perform a reciprocating movement along the known distance between the electronic optical system 106 and the optical microscope unit 108. The optical microscope unit 108 comprises a light source 142, an optical lens 141, and a CCD camera 140. The optical microscope unit 108 detects an optical image of a circuit pattern formed on the object to be inspected, for example, the semiconductor wafer 1, and calculates rotation shift quantity of the circuit pattern based on the optical image detected, thus transmitting the rotation shift quantity calculated to the general control unit 104. This allows the general control unit 104 to amend the rotation shift quantity by, for example, rotating the rotation stage. Also, the general control unit 104 transfers the rotation shift quantity to an amendment control circuit 143. The amendment control circuit 143, based on the rotation shift quantity, amends, for example, a scanning deflection position of the electron beam caused by the scanning deflector 34, thus making it possible to amend the rotation shift. Also, the optical microscope unit 108 detects an optical image of a circuit pattern formed on the object to be inspected, for example, the semiconductor wafer 1, and observes the optical image by, for example, displaying it on a monitor 150. Then, the optical microscope unit 108, based on the optical image observed and using an inputting means, inputs coordinates of an inspected area into the general control unit 104, thereby making it possible to set the inspected area towards the general control unit 104. It also become possible to measure in advance a pitch between chips in the circuit pattern formed on, for example, the semiconductor wafer 1 or a repetition pitch in repetition patterns such as memory cells, and to input it into the general control unit 104. Incidentally, although, in FIG. 11, the optical microscope unit 108 is provided inside the inspection room 105, it is allowable that the optical microscope unit 108 is provided outside the inspection room 105 so as to detect the optical image of the semiconductor wafer 1 through the glass windows.

As shown in FIG. 1 and FIG. 11, the electron beam launched from the electron gun 31, through the condenser lens 32 and the objective lens 33, is narrowed into a beam diameter about a pixel size on a sample surface. At this time, a ground electrode 38 and a retarding electrode 37 apply a negative electric potential to the sample so as to decrease speed of the electron beam between the objective lens 33 and the object to be inspected (the sample) 100, thus aiming at making the resolving power even higher in the low-accelerating voltage region. When irradiated with the electron beam, the object to be inspected (the wafer 1) 100 generates electrons. A two-dimensional electron beam image of the object to be inspected is obtained by a repetition scanning of the electron beam in a X-direction by means of the scanning deflector 34 and by detecting the electrons generated from the object to be inspected 100 in synchronization with a continuous movement of the object to be inspected (the sample) 100 in a Y-direction by means of a stage 2. The electrons generated from the object to be inspected are captured by the detector 35, and amplified by the amplifier 36. At that time, in order to make a high rate inspection possible, it is desirable to employ an electrostatic deflector with a high deflecting speed as the scanning deflector 34 which performs the repetition scanning of the electron beam in a X-direction, to employ a thermal electric field radiation type electron gun, which can shorten an irradiation time because it can increase the electron beam current, and to employ, as the detector 35, a semiconductor detector which allows a high rate driving.

Figure 12:
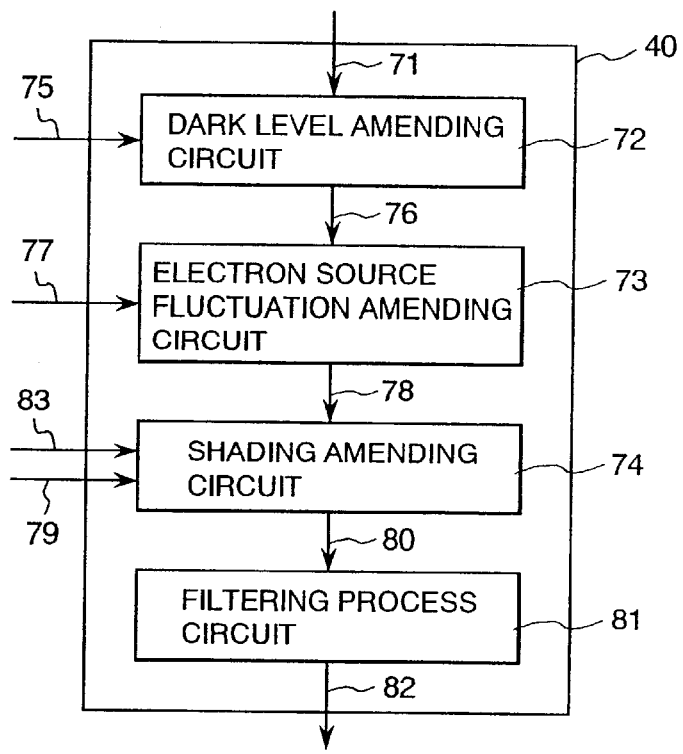
FIG. 12 is a diagram showing a concrete configuration of a preprocessing circuit in connection with the present invention.

Described next, using FIG. 1, FIG. 11, and FIG. 12, is the image fetching unit 102. An electron detection signal detected by the electron detector 35 in the electron detecting unit 107 is amplified by the amplifier 36 and converted into digital image data (gradation image data) by an A/D converter 39. An output of the A/D converter 39 is configured to be transmitted by a light converting means (light emitting device) 123, a transmitting means (optical fiber cable) 124, and an electricity converting means (light receiving device) 125. According to this configuration, it is sufficient for the transmitting means 124 to have the same transmitting rate as that of clock frequency in the A/D converter 39. The output of the A/D converter 39 is converted into an optical digital signal by the light converting means (light emitting device) 123, transmitted through optical transmission by the transmitting means (optical fiber cable) 124, and converted into the digital image data (gradation image data) by the electricity converting means (light receiving device) 125. Namely, the transmission is carried out in such a manner as to be converted into a light signal. The reason is that, in order to guide electrons 52 from the reflector 117 into the semiconductor detector 35, it is required to perform a floating of configuration components from the semiconductor detector 35 to the light converting means 123 (the semiconductor detector 35, the amplifier 36, the A/D converter 39, and the light converting means (light emitting device) 123) up to a positive high electric potential by means of a high voltage power supply (not illustrated). Strictly speaking, it is sufficient to raise only the semiconductor detector 35 up to the positive high electric potential. It is desirable, however, that the amplifier 36 and the A/D converter 39 are located close to the semiconductor detector 35 in order to prevent a mixture of noises and a deterioration of signals. Accordingly, it is difficult to keep only the semiconductor detector 35 raised up to the positive high electric potential, and in the end, the above-mentioned configuration components as a whole are raised up to the high electric potential. Namely, since the transmitting means (optical fiber cable) 124 is formed with a high insulating material, the image signal which was at the positive high electric potential level at the light converting means (light emitting device) 123, after having passed through the transmitting means (optical fiber cable) 124, falls at an earth level, thus making it possible to obtain output of an image signal at the earth level from the electricity converting means (light receiving device) 125.

Figure 13:
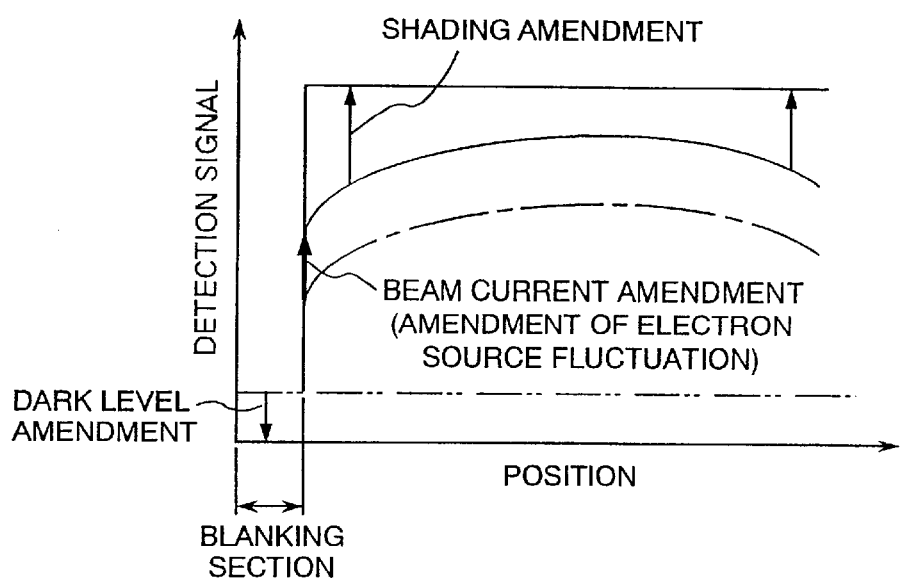
FIG. 13 is a diagram for explaining content to be amended by the preprocessing circuit shown in FIG. 12.

A preprocessing circuit (image amendment circuit) 40 comprises a dark level amending circuit 72, an electron source fluctuation amending circuit 73, a shading amending circuit 74, and soon. Digital image data (gradation image data) 71 obtained by the electricity converting means (light receiving device) 125 undergo, in the preprocessing circuit (image amendment circuit) 40, image amendments such as a dark level amendment, an electron source fluctuation amendment, and a shading amendment. The dark level amendment in the dark level amending circuit 72, as shown in FIG. 13, amends a dark level with reference to a detection signal 71 in a beam-blanking period, which is extracted based on a scanning line synchronization signal 75 obtained from the general control unit 104. Namely, the reference signal for amending the dark level is updated for each line, regarding as the dark level an average of gradation values with, for example, a specific number of pixels at a specific position during the beam-blanking period. In this way, in the dark level amending circuit 72, the dark level amendment is carried out by employing the detection signal, which is detected during the beam-blanking period, as a reference signal to be updated for each line. The electron source fluctuation amendment in the electron source fluctuation amending circuit 73 is performed, as is shown in FIG. 13, by normalizing a detection signal 76, to which the dark level amendment has been made, with the use of a beam electric current 77 monitored by the Faraday cup (not illustrated) for detecting the above-described beam current with an amendment period (for example, 100 kHz of line unit). Since there is no rapid variation in the electron source fluctuation, it is allowable to use a beam current which was detected one to several lines before. As is shown in FIG. 13, the shading amendment in the shading circuit 74 amends, for a detection signal 78 to which the electron source fluctuation amendment has been made, variations in light quantity due to a beam scanning position 79 obtained from the general control unit 104. Namely, the shading amendment performs the amendment (normalization) for each pixel, based on reference illumination data 83 detected in advance. The shading amending reference data 83 are created as follows. Image data detected in advance are once stored in an image memory (for example, a unit 147), and then the image data stored are sent to a computer provided in the general control unit 104 or a host computer connected with the general control unit 104 over a network. The computer provided in the general control unit 104 or the host computer connected with the general control unit 104 over the network processes the sent image data with software, thus creating the shading amending reference data 83. Also, it is allowable that the shading amending reference data 83 are calculated and stored in advance using the host computer connected with the general control unit 104 over the network, and then are downloaded at the time of starting the inspection so that the CPU in the shading amending circuit 74 can capture the downloaded data. In the shading amending circuit 74, there are provided two aspects of amendment memories with the number of pixels in a deflected width of an ordinary electron beam (for example, 1024 pixels). Concerning whole visual field correspondence, the correspondence is achieved by switching each of the memories during the time of executing no inspection (i.e. the time interval from when one visual field inspection is over and the next one visual field inspection is started). Installed as the amendment data are the one with the number of pixels in a maximum deflected width of the electron beam (for example, 5000 pixels). The CPU achieves the correspondence by rewriting the data in each of the amendment memories by the time the next one visual field inspection is over.

As described above, performed to the digital image data (gradation image data) 71 obtained by the electricity converting means (light receiving device) 125 are the following amendments, i.e. the dark level amendment (the dark level is amended with reference to the detection signal 71 during the beam-blanking period), the electron source fluctuation amendment (intensity of the beam current is monitored, and the signal is normalized using the beam current), and the shading amendment (the variations in light quantity due to the beam scanning position are amended). After that, performed to the amended digital image data (gradation image data) 80 in order to improve the image quality is a filtering process in a filtering process circuit 81 by means of a Gaussian filter, an average value filter, and an edge emphasizing filter, and so on. Distortion of the image, if required, is also amended These preprocessings are carried out to convert the detection images so that they will be advantageous and helpful to a defect judging process later.

A delay circuit 41, which comprises units such as shift registers, delays by a constant time an amended digital image data (gradation image data) 82 the image quality of which has been improved by the preprocessing circuit 40. If the delay time, which is obtained from the general control unit 104, is made equal to a time during which, for example, the stage 2 moves by a chip pitch (d1 in FIG. 2), a delayed signal g0 and an undelayed signal f0 become image signals at a same place in chips neighboring to each other. This turns out to be the chip comparison inspection described above. Otherwise, if the delay time, which is obtained from the general control unit 104, is made equal to a time during which the stage 2 moves by a pitch of a memory cell (d2 in FIG. 2), a delayed signal g0 and an undelayed signal f0 become image signals at a same place in memory cells neighboring to each other. This turns out to be the cell comparison inspection described above. In this way, the delay circuit 41 is configured so that it can select an arbitrary delay time by controlling a position of a pixel to be read, based on information obtained from the general control unit 104. As is described above, the digital image data (gradation image data) f0 and g0, which are to be compared with each other, are fetched from the image fetching unit 102. Hereinafter, f0 and g0 are referred to as a detection image and a comparison image, respectively. incidentally, as shown in FIG. 11, it is allowable to store the comparison image signal g0 in a first image memory unit 146 comprising units such as the shift registers and the image memories and to store the detection image signal f0 in a second image memory unit 147 comprising units such as the shift registers and the image memories. As described above, the first image memory unit 146 may comprise the delay circuit 41, and the second image memory unit 147 is not necessarily required.

Also, it is possible to display on the monitor 150 and observe the electron beam images captured in units such as the preprocessing circuit 40 and the second image memory unit 147, or the optical images detected by the optical microscope unit 108.

Describe next, using FIG. 1, is an image processing unit 103*a*.

Obtained from the preprocessing unit 40 is a detection image f0(x,y) represented by a gradation value (a value of light and shade) about an inspection area on the object to be inspected 100. Obtained from the delay circuit 41 is a comparison image (criterion image : reference image) g0(x, y) represented by a gradation value (a value of light and shade) about an inspection area on the object to be inspected 100, which becomes a criterion on which the comparison is made.

Figure 3:
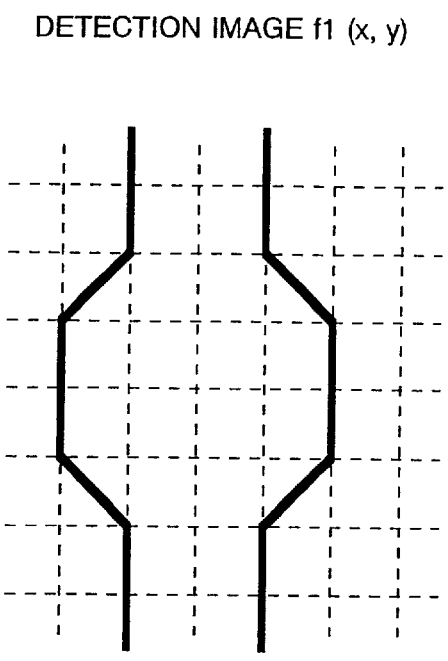
FIG. 3 is a diagram for explaining a sampling error in connection with the present invention.
Figure 3:
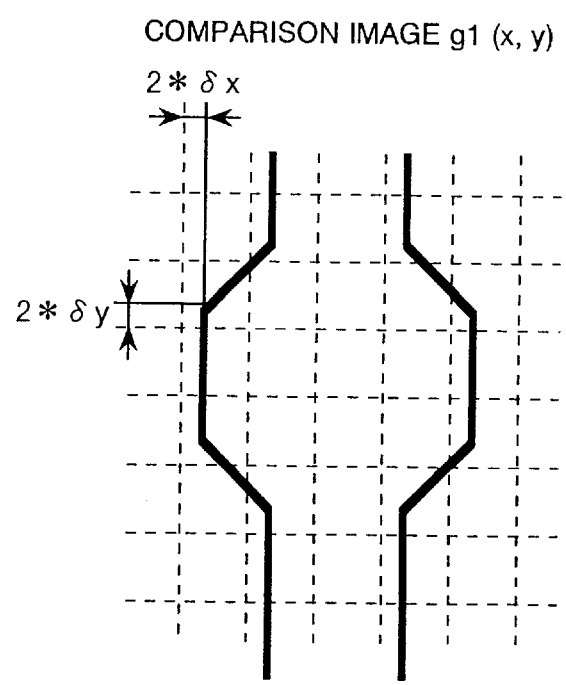

In a pixel unit of position alignment unit 42, a position of, for example, the comparison image is shifted so that a position shift quantity of the comparison image g0(x,y) with reference to the above-mentioned detection image f0(x,y) falls within 0 to 1 pixel, in other words, a position at which "compatibility" (i.e. the degree of matching) between f0(x, y) and g0(x,y) becomes its maximum falls within 0 to 1 pixel. As a result, it turns out that, as shown in FIG. 3, position alignment has been made with one pixel unit or less of accuracy between the detection image f0(x,y) and the comparison image g0(x,y). The pixel is indicated by a square shown by a chain line in FIG. 3. The pixel is a unit which is detected by the electron detector 35, undergoes a sampling by means of the A/D converter 39, and is converted into the digital value (the gradation value: the value of light and shade). Namely, the pixel unit is a minimum unit of the images which can be detected by the electron detector 35. Incidentally, considered as the above-described "compatibility" can be expressions such as the following formula 1, $$\max|f0-g0|, \ \Sigma\Sigma|f0-g0|, \ \Sigma\Sigma(f0-g0)^2 \qquad (1)$$

where max|f0−g0| shows a maximum of absolute value of a difference between the detection image f0(x,y) and the comparison image g0(x,y). $\Sigma\Sigma$|f0−g0| indicates a summation of the difference between the detection image f0(x,y) and the comparison image g0(x,y) within the images. $\Sigma\Sigma$(f0−g0)$^2$ shows a value obtained by integrating in a x-direction and a y-direction a square of the difference between the detection image f0(x,y) and the comparison image g0(x,y).

Content to be processed varies, depending on which of the formula 1 is employed. Shown here is a case in which $\Sigma\Sigma$|f0−g0| is employed.

Assuming that $m_x$ and $m_y$ are shift quantities of the comparison image g0(x,y) in a x-direction and a y-direction, respectively (where $m_x$ and $m_y$ are integers), quantities e1($m_x,m_y$) and s1($m_x,m_y$) are defined as the expressions (2) and (3) described below.

$$e1(m_x,m_y)=\Sigma\Sigma|f0(x,y)-g0(x+m_x,y+m_y)| \qquad (2)$$

$$s1(m_x,m_y)=e1(m_x,m_y)+e1(m_x+1,m_y)+e1(m_x,m_y+1)+e1(m_x+1,m_y+1) \quad (3)$$

In the equation (2), $\Sigma\Sigma$ indicates the summation within the image. What is needed here are values of the shift quantity $m_x$ in a x-direction and the shift quantity $m_y$ in a y-direction at which s1($m_x,m_y$) becomes its minimum. Accordingly, by changing each of $m_x$ and $m_y$ in such a way as ±0, 1, 2, 3, 4 . . . n, in other words, by shifting the comparison image g0(x,y) by the pixel pitch, s1($m_x$, $m_y$) at each time is calculated. Then, values of $m_x0$ and $m_y0$ out of $m_x$ and $m_y$, at which it becomes its minimum, are determined. Additionally, since n is a maximum shift quantity of the comparison image, it is necessary to make, depending on position accuracy of the detecting unit 101, the value of n even larger as the position accuracy gets worse. From the pixel unit of position alignment unit 42, the detection image f0(x,y) is outputted just as it is, and the comparison image g0(x,y) is outputted with shift applied by ($m_x0,m_y0$). Namely, this is expressed by the relations, $$f1(x,y)=f0(x,y), \ g1(x,y)=g0(x+m_x0,y+m_y0).$$

In a one pixel or less of shift detecting unit 43, the images f1(x,y) and g1(x,y), over which the position alignment has been performed in the pixel unit, are divided into small areas (for example, a partial image consisting of 128*256 pixels), and position shift quantity of one pixel or less (the position shift quantity becomes a real number within a range of 0 to 1) is calculated for each divided area (the partial image). The division into the small areas is made in order to correspond to distortions of the images, and it is needed to arrange an area which is small enough to be able to neglect the distortion therein. Employed as a measure of the compatibility can also be the alternatives shown in the formula 1. Shown here is a case in which the third expressions, i.e. "a summation of square of the difference" ($\Sigma\Sigma$(f0−g0)$^2$) is employed.

Assuming that the position shift quantity is equal to zero at an intermediate position between f1(x,y) and g1(x,y), and, as shown in FIG. 3, f1 is shifted by $-\delta x$ in a x-direction and by $-\delta y$ in a y-direction, and g1 is shifted by $+\delta x$ in a x-direction and by $+\delta y$ in a y-direction. Namely, it is considered that the position shift quantity between f1(x,y) and g1(x,y) is $2*\delta x$ in a x-direction and $2*\delta y$ in a y-direction. Since $\delta x$ and $\delta y$ are no integers, it is required to define a value between two pixels in order to shift the images by $\delta x$ or $\delta y$. Defined as the following expressions (4) and (5) are an image f2, which is obtained by shifting f1 by $+\delta x$ in a x-direction and by $+\delta y$ in a y-direction, and an image g2, which is obtained by shifting g1 by $-\delta x$ in a x-direction and by $-\delta y$ in a y-direction.

$$f2(x,y)=f1(x+\delta x,y+\delta y)=f1(x,y)+\delta x(f1(x+1,y)-f1(x,y))+\delta y(f1(x,y+1)-f1(x,y)) \quad (4)$$

$$g2(x,y)=g1(x-\delta x,y-\delta y)=g1(x,y)+\delta x(g1(x-1,y)-g1(x,y))+\delta y(g1(x,y-1)-g1(x,y)) \quad (5)$$

The expressions (4) and (5) are based on so-called a linear interpolation. When employing "a summation of square of the difference", $e2(\delta x, \delta y)$, i.e. the compatibility between f2 and g2 turns out to be the following expression (6).

$$e2(\delta x,\delta y)=\Sigma\Sigma(f2(x,y)-g2(x,y))^2 \quad (6)$$

$\Sigma\Sigma$ is a summation within the small area (the partial area). An object of the one pixel or less of shift detecting unit 43 is to determine values of $\delta x0$ of $\delta x$ and $\delta y0$ of $\delta y$ at which $e2(\delta x, \delta y)$ becomes its minimum. Setting to be zero expressions obtained by partially differentiating the above-mentioned expression (6) with $\delta x$, $\delta y$ and solving them with respect to $\delta x$, $\delta y$, the values have been found to be the formulas (7) and (8) described below.

$$\delta x=\{(\Sigma\Sigma C0*Cy)*(\Sigma\Sigma Cx*Cy)-(\Sigma\Sigma C0*Cx)*(\Sigma\Sigma Cy*Cy)\}/\{(\Sigma\Sigma Cx*Cx)*(\Sigma\Sigma Cy*Cy)-(\Sigma\Sigma Cx*Cy)*(\Sigma\Sigma Cx*Cy)\} \quad (7)$$

$$\delta y=\{(\Sigma\Sigma C0*Cx)*(\Sigma\Sigma Cx*Cy)-(\Sigma\Sigma C0*Cy)*(\Sigma\Sigma Cx*Cx)\}/\{(\Sigma\Sigma Cx*Cx)*(\Sigma\Sigma Cy*Cy)-(\Sigma\Sigma Cx*Cy)*(\Sigma\Sigma Cx*Cy)\} \quad (8)$$

where C0, Cx, and Cy are given by the following relations (9), (10), and (11), respectively.

$$C0=f1(x,y)-g1(x,y) \quad (9)$$

$$Cx=\{f1(x+1,y)-f1(x,y)\}-\{g1(x-1,y)-g1(x,y)\} \quad (10)$$

$$Cy=\{f1(x,y+1)-f1(x,y)\}-\{g1(x,y-1)-g1(x,y)\} \quad (11)$$

In order to determine $\delta x0$ and $\delta y0$, as shown in the formulas (7) and (8), it is required to determine the above-mentioned variety kinds of statistical quantities $\Sigma\Sigma$ Ck*Ck (where Ck=C0, Cx, and Cy). Based on the detection image f1(x,y) and the comparison image g1(x,y) consisting of the gradation values (the values of light and shade), which are obtained from the pixel unit of position alignment unit 42 and over which the position alignment has been performed in the pixel unit, a statistical quantity calculating unit 44 calculates the variety kinds of statistical quantities $\Sigma\Sigma$Ck*Ck.

Using $\Sigma\Sigma$Ck*Ck calculated by the statistical quantity calculating unit 44, a sub CPU executes arithmetic computation of the above-described expressions (7) and (8) so as to determine $\delta x0$ and $\delta y0$.

Delay circuits 46 and 47, which comprise units such as shift registers, delay the image signals f1 and g1 by a time period that the one pixel or less of position shift detecting unit 43 needs to determine $\delta x0$ and $\delta y0$.

Determined by a difference image extracting circuit (a finite difference extracting circuit a distance extracting unit) 49 is sub (x,y), i.e. a difference image (a distance image) between f1 and g1 which has a position shift of $2*\delta x0$ and $2*\delta y0$ in calculation. The difference image (the distance image) sub (x,y) is expressed by the expression (12) as follows.

$$sub(x,y)=g1(x,y)-f1(x,y) \quad (12)$$

Figure 5:
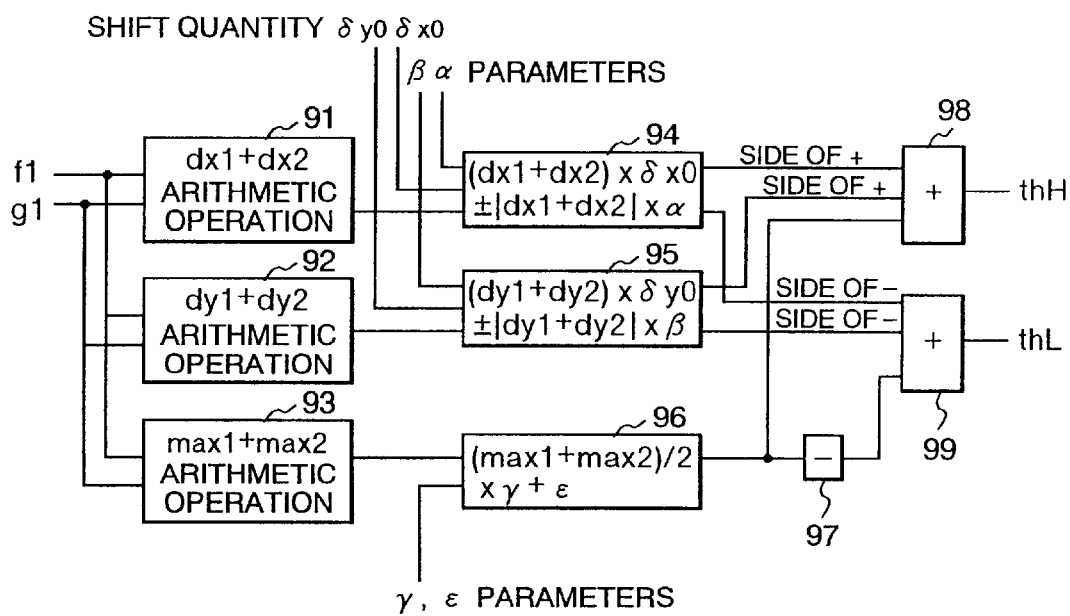
FIG. 5 is a diagram showing a concrete configuration of a threshold arithmetic circuit in connection with the first embodiment of the present invention.

Using the image signals f1 and g1 which have passed through the delay circuits 46 and 47 and the one pixel or less of position shift quantities $\delta x0$ and $\delta y0$ obtained by the one pixel or less of position shift detecting unit 43, a threshold arithmetic circuit (an allowable range arithmetic unit) 48 calculates two threshold values (allowable values indicating allowable range) thH(x, y) and thL(x, y), which a defect judging circuit (a defect judging unit) 50 uses to determine whether or not the pixel is a defective candidate depending on a value of the difference image (the distance image) sub (x, y) obtained from the difference image extracting circuit (the finite difference extracting circuit: the distance extracting unit) 49. Then, thH(x, y) is a threshold value (allowable value indicating allowable range) defining an upper limit of the difference image (the distance image) sub (x, y), and thL(x, y) is a threshold value (allowable value indicating allowable range) defining a lower limit of the difference image (the distance image) sub (x, y). Shown in FIG. 5 is a configuration of the threshold arithmetic circuit 48. Content of the arithmetic operation in the threshold arithmetic circuit 48 is expressed by the expressions (12) and (13) as follows.

$$thH(x,y)=A(x,y)+B(x,y)+C(x,y) \quad (13)$$

$$thL(x,y)=A(x,y)-B(x,y)-C(x,y) \quad (14)$$

Here, A(x,y) is a term which is given by the following relation (15) and has a function of substantially amending the threshold values with the use of the one pixel or less of position shift quantities $\delta x0$ and $\delta y0$ in correspondence with a value of the difference image (the distance image) sub (x,y).

Also, B(x,y) is a term which is given by the following relation (16) and has a function of allowing an infinitesimal position shift of pattern edges (an infinitesimal difference in the pattern configuration and distortion in the patterns are attributed to the infinitesimal position shift of pattern edges from a local point of view) between the detection image f1 and the comparison image g1.

C(x,y) is a term which is given by the following relation (17) and has a function of allowing an infinitesimal difference in the gradation value (the value of light and shade) between the detection image f1 and the comparison image g1.

$$A(x,y)=\{dx1(x,y)*\delta x0-dx2(x,y)*(-\delta x0)\}+\{dy1(x,y)*\alpha y0-dy2(x,y)*(-\delta y0)\}=\{dx1(x,y)+dx2(x,y)\}*\delta x0+\{dy1(x,y)+dy2(x,y)\}*\delta y0 \quad (15)$$

$$B(x,y)=|\{dx1(x,y)*\alpha-dx2(x,y)*(-\alpha)\}|+|\{dy1(x,y)*\beta-dy2(x,y)*(-\beta)\}|=|\{dx1(x,y)+dx2(x,y)\}*\alpha|+|\{dy1(x,y)+dy2(x,y)\}*\beta| \quad (16)$$

$$C(x,y)=((max1+max2)/2)*\gamma+\epsilon \quad (17)$$

Where $\alpha$ and $\beta$ are real numbers within a range of 0 to 0.5, $\gamma$ is a real number greater than zero, and $\epsilon$ is an integer greater than zero.

Also, dx1(x,y), which is given by the following relation (18), indicates a variation amount in the gradation value (the value of light and shade) in the detection image f1(x,y)

between an image and an image which is +1 proximate thereto in a x-direction, dx2(x,y), which is given by the following relation (19), indicates a variation amount in the gradation value (the value of light and shade) in the detection image g1(x,y) between an image and an image which is −1 proximate thereto in a x-direction, dy1(x,y), which is given by the following relation (20), indicates a variation amount in the gradation value (the value of light and shade) in the detection image f1(x,y) between an image and an image which is +1 proximate thereto in a y-direction, and dy2(x,y), which is given by the following relation (21), indicates a variation amount in the gradation value (the value of light and shade) in the detection image g1(x,y) between an image and an image which is −1 proximate thereto in a y-direction.

$$dx1(x,y)=f1(x+1,y)-f1(x,y) \tag{18}$$

$$dx2(x,y)=g1(x,y)-g1(x-1,y) \tag{19}$$

$$dy1(x,y)=f1(x,y+1)-f1(x,y) \tag{20}$$

$$dy2(x,y)=g1(x,y)-g1(x,y-1) \tag{21}$$

Also, max1, which is given by the following relation (22), indicates a maximum in the gradation value (the value of light and shade) in the detection image f1(x,y) among an image, an image which is +1 proximate thereto in a x-direction, and an image which is +1 proximate thereto in a y-direction, and max2, which is given by the following relation (23), indicates a maximum in the gradation value (the value of light and shade) in the comparison image g1(x,y) among an image, an image which is −1 proximate thereto in a x-direction, and an image which is −1 proximate thereto in a y-direction.

$$max1=max\{f1(x,y),f1(x+1,y),f1(x,y+1),f1(x+1,y+1)\} \tag{22}$$

$$max2=max\{g1(x,y),g1(x-1,y),g1(x,y-1),g1(x-1,y-1)\} \tag{23}$$

Described first is the first term A(x,y) in the expressions (13) and (14) for calculating the threshold values thH(x,y) and thL(x,y). Namely, the first term A(x,y) in the expressions (13) and (14) for calculating the threshold values thH(x,y) and thL(x,y) is a term for amending the threshold values in correspondence with the one pixel or less of position shift quantities δx0 and δy0 determined by the one pixel or less of position shift detecting unit 43. Since, for example, dx1 expressed in the expression (18) is a local variation rate in the gradation value of f1 in a x-direction, dx1(x,y)* δx0 shown in the expression (15) can be said to be a predicted value of a variation in the gradation value (the value of light and shade) of f1 when the position is shifted by δx0. Consequently, the first term {dx1(x,y)*δx0−dx2(x,y)*(−δx0)} shown in the expression (15) can be said to be a value of predicting to what extent the gradation value (the value of light and shade) of the difference image (the distance image) between f1 and g1 is varied for each pixel when the position of f1 is shifted by δx0 and the position of g1 is shifted by −δx0 in a x-direction. Similarly, the second term can be said to be a value of the prediction about a y-direction. Namely, {dx1(x,y)+dx2(x,y)} *δx0 is a value of predicting to what extent the gradation value (the value of light and shade) of the difference image (the distance image) between f1 and g1 is varied for each pixel in a x-direction when {dx1(x,y)+dx2(x,y)}, i.e. a local variation rate in the difference image (the distance image) between the detection image f1 and the comparison image g1 in a x-direction, is multiplied by the position shift δx0. Similarly, {dy1(x,y)+dy2(x,y)}*δy0 is a value of predicting to what extent the gradation value (the value of light and shade) of the difference image (the distance image) between f1 and g1 is varied for each pixel in a y-direction when {dy1(x,y)+dy2(x,y)}, i.e. a local variation rate in the difference image (the distance image) between the detection image f1 and the comparison image g1 in a y-direction, is multiplied by the position shift δy0.

As explained above, the first term A(x,y) in the expressions for the threshold values thH(x,y) and thL(x,y) is a term for canceling the known position shift quantities δx0 and δy0.

Described next is the second term B(x,y) in the expressions (13) and (14) for calculating the threshold values thH(x,y) and thL(x,y). Namely, the second term B(x,y) in the expressions (13) and (14) for calculating the threshold values thH(x,y) and thL(x,y) is a term for allowing an infinitesimal position shift of pattern edges (an infinitesimal difference in the pattern configuration and distortion in the patterns are attributed to the infinitesimal position shift of pattern edges from a local point of view). As is apparent from the comparison between the expression (15) for determining A(x,y) and the expression (16) for determining B(x,y), B(x,y) is an absolute value of the predicted variation in the gradation value (the value of light and shade) of the difference image (the distance image) by means of the position shifts δx0 and δy0. If it is assumed that A(x,y) cancels the position shifts, adding B(x,y) to A(x,y) means the following. From a state in which the positions coincides with each other, the positions are shifted by α in a x-direction and by β in a y-direction, taking into consideration the infinitesimal position shift of the pattern edges caused by an infinitesimal difference due to the pattern configuration and the distortion in the patterns. Namely, +B(x,y) shown in the above-mentioned expression (13) allows +α in a x-direction and +β in a y-direction as the infinitesimal position shift of the pattern edges caused by an infinitesimal difference due to the pattern configuration and the distortion in the patterns. Also, as shown in the above-mentioned expression (14), subtracting B(x,y) from A(x,y) means that, from the state in which the positions coincides with each other, the positions are further shifted by −α in a x-direction and by −β in a y-direction. Namely, −B(x,y) shown in the above-mentioned expression (14) allows the position shifts by −α in a x-direction and by −β in a y-direction, respectively. After all, as shown in the above-mentioned expressions (13) and (14), the position shift by ±α and ±β are allowed by providing the threshold with the upper limit thH(x,y) and the lower limit thL(x,y). Moreover, in the threshold arithmetic circuit 48, values of the parameters α and β inputted are set to be appropriate values. This makes it possible to freely control the allowed position shift quantities caused by an infinitesimal difference due to the pattern configuration and the distortion in the patterns (the infinitesimal position shift of the pattern edges).

Described next is the third term C(x,y) in the expressions (13) and (14) for calculating the threshold values thH(x,y) and thL(x,y). Namely, the third term C(x,y) in the expressions (13) and (14) for calculating the threshold values thH(x,y) and thL(x,y) is a term for allowing an infinitesimal difference in the gradation value (the value of light and shade) between the detection image f1 and the comparison image g1. As shown in the expression (13), what the addition of C(x,y) means is to allow that the gradation value (the value of light and shade) of the comparison image g1 is greater by C(x,y) than the gradation value (the value of light and shade) of the detection image f1. As shown in the expression (14), what the subtraction of C(x,y) means is to allow that the gradation value (the value of light and shade) of the comparison image g1 is smaller by C(x,y) than the gradation value (the value of light and shade) of the detection image f1. In the present invention, as shown in the expression (17), C(x,y) is set to be a summation of a constant $\epsilon$ and a value obtained by multiplying a representative value of the gradation value in the local area (a maximum value here) by a proportionality constant $\gamma$. There is no need of sticking to this function, however. As long as the way the gradation value varies is known, it is much better to select a function suitable therefor. If, for example, it is known that a width of the variation is proportional to a square root of the gradation value, the expression (17) should be replaced by the expression C(x,y)=(square root of (max1+max2))*$\gamma$+$\epsilon$. In the threshold arithmetic circuit 48, as is the case with B(x,y), it becomes possible to freely control the difference in the allowed gradation value (the value of light and shade) by setting values of the parameters $\gamma$ and $\epsilon$ to be appropriate values.

The threshold arithmetic circuit (allowable range arithmetic unit) 48, as shown in FIG. 5, comprises an arithmetic circuit 91 which, based on the detection image f1(x,y) consisting of the gradation value (the value of light and shade) inputted from the delay circuit 46 and the comparison image g1(x,y) consisting of the gradation value (the value of light and shade) inputted from the delay circuit 47, performs an arithmetic operation of {dx1(x,y)+dx2(x,y)} using the expressions (18) and (19), an arithmetic circuit 92 which performs an arithmetic operation of {dy1(x,y)+dy2(x,y)} using the expressions (20) and (21), and an arithmetic circuit 93 which performs an arithmetic operation of (max1+max2) using the expressions (22) and (23). The threshold arithmetic circuit 48 further comprises an arithmetic circuit 94 which, based on {dx1(x,y)+dx2(x,y)} obtained by the arithmetic circuit 91, $\delta$x0 obtained by the one pixel or less of position shift detecting unit 43, and a parameter $\alpha$ to be inputted, performs an arithmetic operation of ({dx1(x,y)+dx2(x,y)}*$\delta$x0±|{dx1(x,y)+dx2(x,y)}|*$\alpha$), i.e. a portion of the expression (15) and a portion of the expression (16), an arithmetic circuit 95 which, based on {dy1(x,y)+dy2(x,y)} obtained by the arithmetic circuit 92, $\delta$y0 obtained by the one pixel or less of position shift detecting unit 43, and a parameter $\beta$ to be inputted, performs an arithmetic operation of ({dy1(x,y)+dy2(x,y)}*$\delta$y0±|{dy1(x,y)+dy2(x,y)}|*$\beta$), i.e. a portion of the expression (15) and a portion of the expression (16), and an arithmetic circuit 96 which, based on (max1+max2) obtained by the arithmetic circuit 93 and parameters $\gamma$ and $\epsilon$ to be inputted, performs an arithmetic operation of ((max1+max2)/2)*$\gamma$+$\epsilon$) following, for example, the expression (17). The threshold arithmetic circuit 48 still further comprises an adding circuit 98 which outputs the upper limit of the threshold thH(x,y) by performing+ arithmetic operation of ({dx1(x,y)+dx2(x,y)}*$\delta$x0+|{dx1(x,y)+dx2(x,y)}|*$\alpha$) obtained by the arithmetic circuit 94, ({dy1(x,y)+dy2(x,y)}*$\delta$y0+|{dy1(x,y)+dy2(x,y)}|*$\beta$) obtained by the arithmetic circuit 95, and ((max1+max2)/2)*$\gamma$+$\epsilon$) obtained by the arithmetic circuit 96, a subtracting circuit 97 which performs – arithmetic operation of ((max1+max2)/2)*$\gamma$+$\epsilon$) obtained by the arithmetic circuit 96, and an adding circuit 99 which outputs the lower limit of the threshold thL(x, y) by performing + arithmetic operation of ({dx1(x,y)+dx2(x,y)}*$\delta$x0–|{dx1(x, y)+dx2(x, y)}|*$\alpha$) obtained by the arithmetic circuit 94, ({dy1(x,y)+dy2(x,y)}*$\delta$y0–|{dy1(x,y)+dy2(x,y)}|*$\beta$) obtained by the arithmetic circuit 95, and –((max1+max2)/2)*$\gamma$+$\epsilon$) obtained by the subtracting circuit 97.

Incidentally, the threshold arithmetic circuit 48 can also be embodied by the CPU through a soft processing thereof. It is also allowable that the parameters to be inputted into the threshold arithmetic circuit 48 are inputted by using an inputting means provided in the general control unit 104 (for example, an inputting means comprising a keyboard, a recording medium, a network, and so on).

Using the difference image (the distance image) sub (x,y) obtained from the difference image extracting circuit (the finite difference extracting circuit) 49, the threshold value at the lower limit thL(x,y) (an allowable value indicating the lower limit within the allowable range) and the threshold value at the upper limit thH(x,y) (an allowable value indicating the upper limit within the allowable range) obtained from the threshold arithmetic circuit 48, the defect judging circuit (the defect judging unit) 50 judges a pixel at the position (x,y), if the following relation (24) is satisfied, to be an non-defective candidate, and the pixel at the position (x,y), if the following relation (24) is not satisfied, to be a defective candidate. The defect judging circuit 50 outputs, for the non-defective candidate pixel, def(x,y) having a value of, for example, zero, and outputs, for the defective candidate pixel, def(x,y) having a value of, for example, one or more indicating the mismatched quantity.

$$\text{thL}(x,y) \leq \text{sub}(x,y) \leq \text{thH}(x,y) \tag{24}$$

In a characteristic extracting circuit 50a, after a noise-like (for example, all of the 3×3 pixels are not the defective candidate pixels at the same time) output is eliminated by a noise eliminating process (For example, a processing of downsizing/upsizing for def(x,y) is performed. For example, when all of the 3×3 pixels are not the defective candidate pixels at the same time, a pixel in the center thereof is made equal to zero (the non-defective candidate pixel) and eliminated by performing the downsizing process, and then it is restored back to the original by performing the upsizing process.), a merge processing of the defective candidate parts, which summarizes the neighboring defective candidate parts into a group, is carried out. After that, the characteristic extracting circuit 50a calculates and outputs, for each group, characteristic quantities 88 such as a coordinate of the center of gravity, XY projection length (This quantity shows maximum lengths in a x-direction and a y-direction. Additionally, a square root of (a square of X projection length+a square of Y projection length) becomes the maximum length), and the area.

As explained above, obtained from the controlled by the general control unit 104 are the characteristic quantities 88 (for example, the coordinate of the center of gravity, the XY projection length, the area, and so on) of the defective candidate parts in correspondence with coordinates on the object to be inspected (sample) 100 irradiated with an electron beam and detected by the electron detector 35.

The general control unit 104 converts position coordinates of the defective candidate parts on the detection image into coordinate system on the object to be inspected (sample) 100 and deletes pseudo defects, finally summarizing data on the defects consisting of the positions on the object to be inspected (sample) 100 and the characteristic quantities calculated by the characteristic extracting circuit 50a in the image processing unit 103a.

The present embodiment allows a position shift of a small area (the partial image) as a whole, an infinitesimal position shift of an individual pattern edge, and an infinitesimal difference in the gradation value (the value of light and shade). This prevents a possibility of misjudging the normal part to be a defect. Also, it becomes possible to freely control allowable values of the position shifts and variations in the gradation values by setting the parameters α, β, γ and ε to be appropriate values.

Also, in the present embodiment, unlike the above-described prior art (Japanese Laid-Open Patent Publication No. Hei 3-177040), it is not carried out to generate, by employing interpolation, images the positions of which coincide with each other in a pseudo way. This prevents a smoothing effect of the images, which is difficult to avoid in the interpolation, and thus brings about an merit of making it advantageous to detect an infinitesimal defect. Actually, the inventors et al. has made the following experiment. After the images the positions of which coincide with each other in a pseudo way are generated by the interpolation with the use of a result of the one pixel or less of position shift detection, a defect judgment is made by, as is the case with the present embodiment, calculating the threshold values allowing the position shifts and variations in the gradation values. Eventually, the experiment has shown a 5% or more of increase in performance of detecting a defect, when comparing a result obtained in the above-mentioned manner with a result obtained by making a defect judgment according to the present embodiment.

Modifications of the First Embodiment

Figure 6:
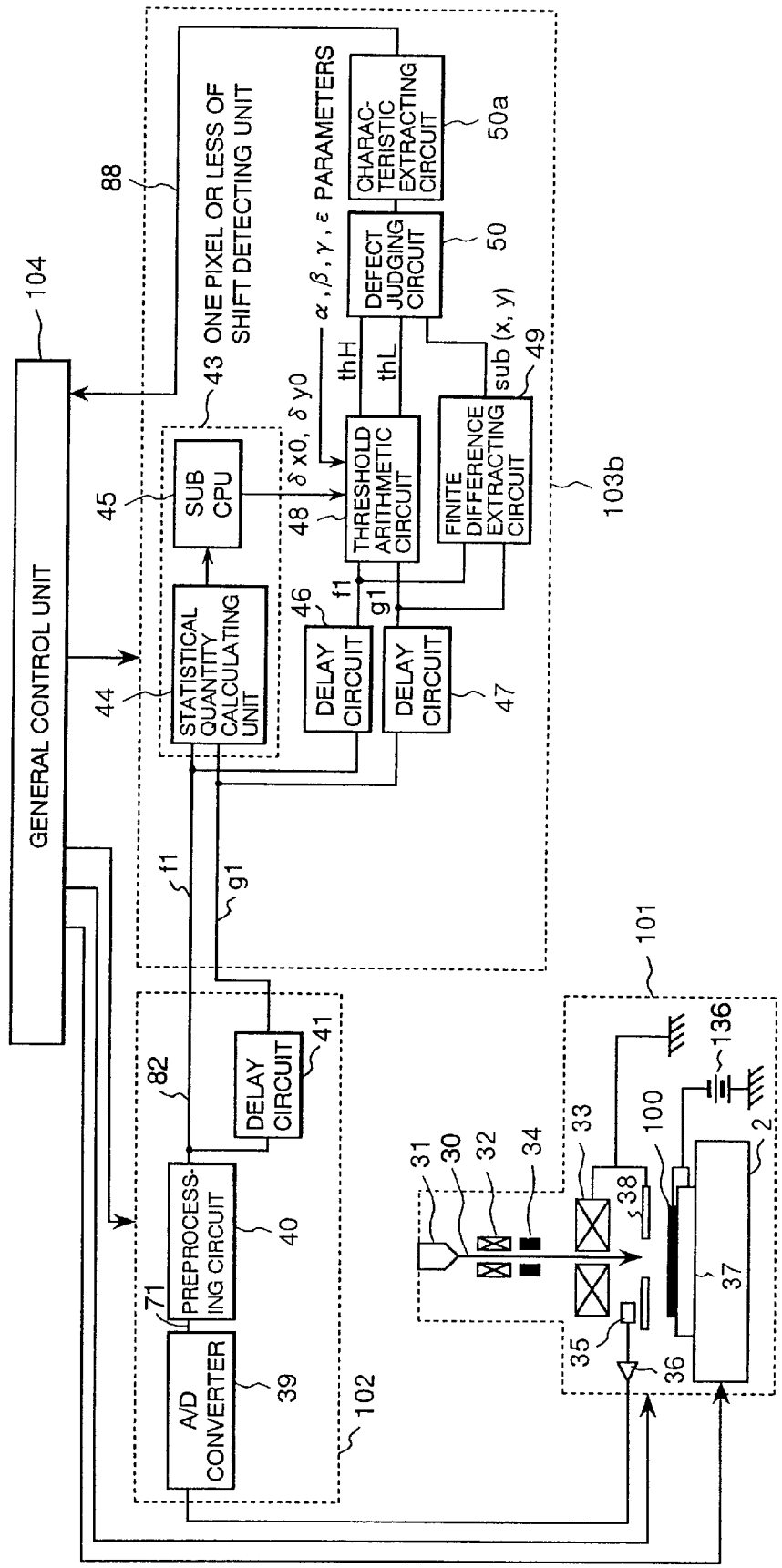
FIG. 6 is a diagram for explaining a first modification in the first embodiment shown in FIG. 1.

In a first modification of the first embodiment, as shown in FIG. 6, no pixel unit of position alignment is performed. When the detecting unit 101 detects an image with a high position accuracy and a position error of the detected image is less than one pixel, the pixel unit of position alignment is unnecessary, and one pixel or less of position shift detection should be performed immediately. Namely, the configuration in which the first modification shown in FIG. 6 differs from the first embodiment shown in FIG. 1 is that, since the detecting unit 101 detects an image with a high position accuracy and a position error of the detected image is less than one pixel, there is provided an image processing unit 103b without the pixel unit of position alignment unit 42. In the first modification, too, the threshold arithmetic circuit 48 outputs a threshold value at an upper limit thH(x,y) (an allowable value indicating the upper limit within an allowable range) based on the equation (13) and a threshold value at a lower limit thL(x,y) (an allowable value indicating the lower limit within an allowable range) based on the equation (14). Using the difference image (the distance image) sub (x,y) obtained from the difference image extracting circuit (the finite difference extracting circuit) 49, the threshold value at the lower limit thL(x,y) (an allowable value indicating the lower limit within the allowable range) and the threshold value at the upper limit thH(x,y) (an allowable value indicating the upper limit within the allowable range) obtained from the threshold arithmetic circuit 48, the defect judging circuit (the defect judging unit) 50 judges a pixel at the position (x,y), if the above-mentioned relation (24) is satisfied, to be an non-defective candidate, and the pixel at the position (x,y), if the above-mentioned relation (24) is not satisfied, to be a defective candidate. The defect judging circuit 50 outputs, for the non-defective candidate pixel, def(x,y) having a value of, for example, zero, and outputs, for the defective candidate pixel, def(x,y) having a value of, for example, one or more indicating the mismatched quantity. Moreover, in the characteristic extracting circuit 50a, after a noise-like output is eliminated by a noise eliminating process (For example, a processing of downsizing/upsizing for def(x,y) is performed.), a merge processing of the defective candidate parts, which summarizes the neighboring defective candidate parts into a group, is carried out.

After that, the characteristic extracting circuit 50a calculates and outputs, for each group, characteristic quantities 88 such as the coordinate of the center of gravity, the XY projection length, and the area.

Figure 7:
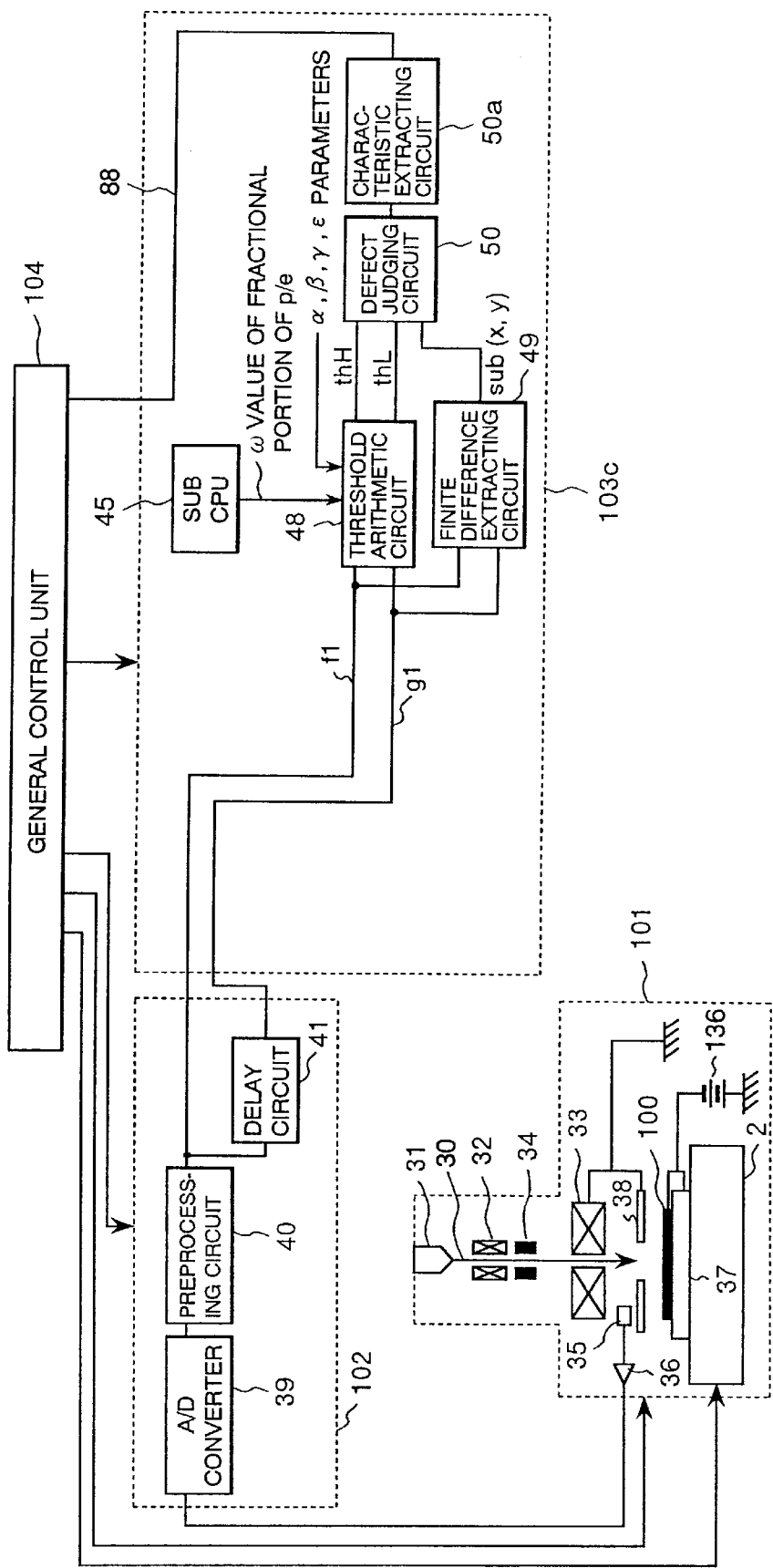
FIG. 7 is a diagram for explaining a second modification in the first embodiment shown in FIG. 1.

In a second modification of the first embodiment, as shown in FIG. 7, neither the pixel unit of position alignment or the one pixel or less of position shift detection is performed. When the detecting unit 101 detects an image with an even higher position accuracy and a position error of the detected image is substantially negligible, even the one pixel or less of position shift detection becomes unnecessary. Namely, the configuration in which the second modification shown in FIG. 7 differs from the first embodiment shown in FIG. 1 is that, since the detecting unit 101 detects an image with an even higher position accuracy and a position error of the detected image is substantially negligible, there are removed the pixel unit of position alignment unit 42 and the one pixel or less of position shift detecting unit 43. Instead, there is provided an image processing unit 103c having a sub CPU 45. The sub CPU 45 outputs ω, i.e. a fractional portion of a value obtained by dividing a comparison interval P by a pixel size e, which is introduced from the general control unit 140. It is assumed that P designates a comparison interval between the images (in the case of the chip comparison, an interval between the chips to be compared, and in the case of the cell comparison, an interval between the memory cells to be compared), e designates a pixel size, and ωx and ωy designate a fractional portion of a value obtained by dividing the comparison interval P by the pixel size e. In this case, δx and δy, which are obtained as the result of the one pixel or less of position shift detection, are replaced by ωx/2 and ωy/2. Namely, it becomes necessary to obtain A(x, y), using the following expression (15').

$$A(x,y)=\{dx1(x,y)*\omega x/2-dx2(x,y)*(-\omega x/2)\}+\{dy1(x,y)*\omega y/2-dy2(x,y)*(-\omega y/2)\}=\{dx1(x,y)+dx2(x,y)\}*\omega x/2+\{dy1(x,y)+dy2(x,y)\}*\omega y/2 \quad (15')$$

In the second modification, too, the threshold arithmetic circuit 48 outputs a threshold value at an upper limit thH(x,y) (an allowable value indicating the upper limit within an allowable range) based on the equation (13) and a threshold value at a lower limit thL(x,y) (an allowable value indicating the lower limit within an allowable range) based on the equation (14). Using the difference image (the distance image) sub (x,y) obtained from the difference image extracting circuit (the finite difference extracting circuit) 49, the threshold value at the lower limit thL(x,y) (an allowable value indicating the lower limit within the allowable range) and the threshold value at the upper limit thH(x,y) (an allowable value indicating the upper limit within the allowable range) obtained from the threshold arithmetic circuit 48, the defect judging circuit (the defect judging unit) 50 judges a pixel at the position (x,y), if the above-mentioned relation (24) is satisfied, to be an non-defective candidate, and the pixel at the position (x,y), if the above-mentioned relation (24) is not satisfied, to be a defective candidate. The defect judging circuit 50 outputs, for the non-defective candidate pixel, def(x,y) having a value of, for example, zero, and outputs, for the defective candidate pixel, def(x,y) having a value of, for example, one or more indicating the mismatched quantity. Moreover, in the characteristic extracting circuit 50a, after a noise-like output is eliminated by a noise eliminating process (For example, a processing of downsizing/upsizing for def(x,y) is performed.), a merge processing of the defective candidate parts, which summarizes the neighboring defective candidate parts into a group, is carried out. After that, the characteristic extracting circuit

50a calculates and outputs, for each group, characteristic quantities 88 such as the coordinate of the center of gravity, the XY projection length, and the area.

In a third modification of the first embodiment, the one pixel or less of position shift quantity is determined in the following way, instead of determining them as shown in the expressions (4) to (11). Determined first are a summation (an extent over which the summation is taken is the one for each small area) of square of a difference in the gradation values (the values of light and shade) of the image f1 and the image g1 in a state in which the position alignment has been performed between f1 and g1 for each pixel, and a summation (an extent over which the summation is taken is the one for each small area) of square of the difference when g1 is shifted with reference to f1 in a variety of directions by an integer multiple of the pixel. Defined next, based on interpolation between theses summations, is a summation of square of the difference when g1 is shifted with reference to f1 by one pixel or less of arbitrary quantity. Employed as the position shift quantity to be calculated is a shift quantity to which the summation defined turns out to be its minimum. Otherwise, used instead of the summation of square of the difference are a summation of absolute value of the difference or a normalized correlation.

A fourth modification of the first embodiment is a modification concerning a calculating method on the expressions (13) to (23).

The expressions (18) to (21) are replaced by the following expressions (25) to (28).

$$dx1(x,y)=[\{f1(x+1,y)+f1(x+1,y+1)\}-\{f1(x,y)+f1(x,y+1)\}]/2 \quad (25)$$

$$dx2(x,y)=[\{g1(x,y)+g1(x,y-1)\}-\{g1(x-1,y)+g1(x-1,y-1)\}]/2 \quad (26)$$

$$dy1(x,y)=[\{f1(x,y+1)+f1(x+1,y+1)\}-\{f1(x,y)+f1(x+1,y)\}]/2 \quad (27)$$

$$dy2(x,y)=[\{g1(x,y)+g1(x-1,y)\}-\{g1(x,y-1)+f1(x-1,y-1)\}]/2 \quad (28)$$

Otherwise, the expressions (18) to (21) are replaced by the following expressions (29) to (30).

$$dx1(x,y)=dy1(x,y)=\max\{f1(x,y), f1(x+1,y), f1(x,y+1), f1(x+1, y+1)\}-\min\{f1(x,y), f1(x+1,y), f1(x,y+1), f1(x+1, y+1)\} \quad (29)$$

$$dx2(x,y)=dy2(x,y)=\max\{g1(x,y), g1(x-1,y), g1(x,y-1), g1(x-1,y-1)\}-\min\{g1(x,y), g1(x-1,y), g1(x,y-1), g1(x-1, y-1)\} \quad (30)$$

Otherwise, the expression (16) is replaced by the following expression (31).

$$B(x,y)=\text{square root of } [\{(dx1(x,y)+dx2(x, y))*\alpha)\}^2+\{(dy1(x,y)+dy2(x,y))*\beta)\}^2] \quad (31)$$

If an position shift of a pattern edge in a x-direction and that of a pattern edge in a y-direction are independent events with each other, the expression (31) should bring about a higher accuracy than the expression (16) does. Compared with the expression (16), however, the expression (31) causes a problem of making scale of the hard ware larger. Accordingly, it is advisable to employ the expression (31) only when the higher accuracy is so much desirable even if the scale of the hard ware becomes larger.

Otherwise, the expression (17) is replaced by the following expressions (32) to (34).

$$C(x,y)=((ave1+ave2)/2)*\gamma+\epsilon \quad (32)$$

where $$ave1=\{f1(x,y)+f1(x+1,y)+f1(x,y+1)+f1(x+1,y+1)\}/4 \quad (33)$$

$$ave2=\{g1(x,y)+g1(x-1,y)+g1(x,y-1)+g1(x-1,y-1)\}/4 \quad (34)$$

Otherwise, instead of the expression (17), the sub CPU 45 prepares in advance a look-up table for a representative gradation value of quantities such as max1 (refer to the expression (22)), max2 (refer to the expression (23)), ave1 (refer to the expression (33)), and ave2 (refer to the expression (34)). Then, the threshold arithmetic circuit 48 determines C(x,y), following the look-up table. It would be sometimes difficult to represent the way the gradation value varies in terms of mathematical functions, depending on the kind of the image detecting system. In that case, it is convenient to employ a method using the look-up table.

Otherwise, the expressions (13) and (14) are replaced by the following expressions (35) and (36).

$$thH(x,y)=A(x,y)+\text{square root of } \{(B(x,y)^2+C(x,y)^2\} \quad (35)$$

$$thL(x,y)=A(x,y)-\text{square root of } \{(B(x,y)^2+C(x,y)^2\} \quad (36)$$

If an infinitesimal position shift of an individual pattern edge and a variation in the gradation value are independent events with each other, the expressions (35) and (36) should bring about a higher accuracy than the expressions (13) and (14) do. Compared with the former, however, the latter causes a problem of making scale of the hard ware larger. Accordingly, it is advisable to employ the latter only when the higher accuracy is so much desirable even if the scale of the hard ware becomes larger.

Second Embodiment

Figure 8:
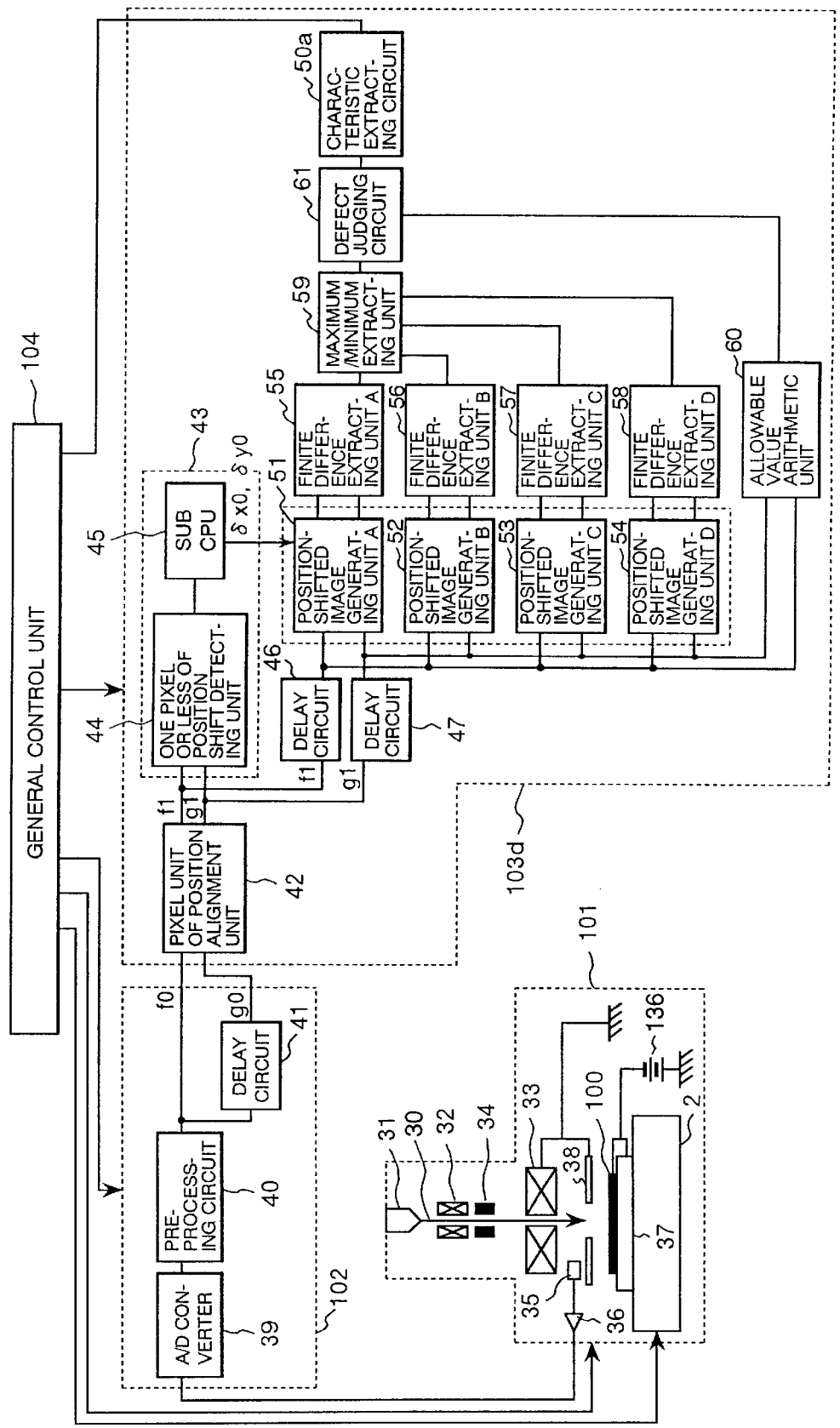
FIG. 8 is a schematic configuration diagram showing a second embodiment of a method of inspecting a pattern and an apparatus thereof in which an electron microscope according to the present invention is employed.

Described below, using FIG. 8, is a second embodiment of a method of inspecting a pattern and an apparatus thereof in connection with the present invention. The present embodiment, as is the case with the first embodiment, comprises a detecting unit 101, an image fetching unit 102, an image processing unit 103d, and a general control unit 104 for controlling the whole system. The detecting unit 101, the image fetching unit 102, and the general control unit 104 are the same as those in the first embodiment. Concerning the image processing unit 103d, too, the configuration and the function are the same as those in the first embodiment by the time one pixel or less of position shift quantities δx and δy are calculated in a one pixel or less of position shift detecting unit 43.

In a position-shifted image generating unit A51, a position-shifted image generating unit B52, a position-shifted image generating unit C53, and a position-shifted image generating unit D54, taking as a center the position relationship in which a detection image f1 and a comparison image g1 to be compared coincide with each other best in calculation, that is, the position relationship in which the detection image f1 is shifted by +δx and +δy and the comparison image g1 is shifted by −δx and −δy, new images are generated by shifting the detection image f1 and the comparison image g1 further in a variety of directions to each other. It is assumed that α designates a position shift quantity in a x-direction and β designates a position shift quantity in a y-direction (α and β are real numbers in a range of 0 to 0.5).

Namely, generated are f2A (an image generated by shifting f1 by +α in a x-direction), g2A (an image generated by shifting g1 by −α in a x-direction), f2B (an image generated by shifting f1 by −α in a x-direction), g2B (an image generated by shifting g1 by +α in a x-direction), f2C (an image generated by shifting f1 by +β in a y-direction), g2C (an image generated by shifting g1 by −β in a y-direction), f2D (an image generated by shifting f1 by −β in a y-direction), and g2D (an image generated by shifting g1 by +β in a y-direction). At that time, since δx, δy, α and β are each no integers, it is required to create shifted images in some way. A variety kinds of methods are known about the generation of the images. Shown here is a case in which the images are generated using the interpolation.

$$f2A(x,y)=f1(x+\delta x0+\alpha,y+\delta y0)=f1(x,y)+(\delta x0+\delta)\{f1(x+1,y)-f1(x,y)\}+\delta y0\{f1(x,y+1)-f1(x,y)\} \quad (37)$$

$$g2A(x,y)=g1(x-\delta x0-\alpha,y-\delta y0)=g1(x,y)+(\delta x0+\alpha)\{g1(x-1,y)-g1(x,y)\}+\delta y0\{g1(x,y-1)-g1(x,y)\} \quad (38)$$

$$f2B(x,y)=f1(x+\delta x0-\alpha,y+\delta y0)=f1(x,y)+(\delta x0-\alpha)\{f1(x+1,y)-f1(x,y)\}+\delta y0\{f1(x,y+1)-f1(x,y)\} \quad (39)$$

$$g2B(x,y)=g1(x-\delta x0+\alpha,y-\delta y0)=g1(x,y)+(\delta x0-\alpha)\{g1(x-1,y)-g1(x,y)\}+\delta y0\{g1(x,y-1)-g1(x,y)\} \quad (40)$$

$$f2C(x,y)=f1(x+\delta x0,y+\delta y0+\beta)=f1(x,y)+\delta x0\{f1(x+1,y)-f1(x,y)\}+(\delta y0+\beta)\{f1(x,y+1)-f1(x,y)\} \quad (41)$$

$$g2C(x,y)=g1(x-\delta x0,y-y0-\beta)=g1(x,y)+\delta x0\{g1(x-1,y)-g1(x,y)\}+(\delta y0+\beta)\{g1(x,y-1)-g1(x,y)\} \quad (42)$$

$$f2D(x,y)=f1(x+\delta x0,y+\delta y0-\beta)=f1(x,y)+\delta x0\{f1(x+1,y)-f1(x,y)\}+(\delta y0-\beta)\{f1(x,y+1)-f1(x,y)\} \quad (43)$$

$$g2D(x,y)=g1(x-\delta x0,y-\delta y0+\beta)=g1(x,y)+\delta x0\{g1(x-1,y)-g1(x,y)\}+(\delta y0-\beta)\{g1(x,y-1)-g1(x,y)\} \quad (44)$$

Determined by a difference image extracting unit A55, based on the following expression (45), is sub A, i.e. a difference image between g2A(x,y) and f2A(x,y) which are outputted from the pixel-shifted image generating unit A51. Determined by a difference image extracting unit B56, based on the following expression (46), is sub B, i.e. a difference image between g2B(x,y) and f2B(x,y) which are outputted from the pixel-shifted image generating unit B52. Determined by a difference image extracting unit C57, based on the following expression (47), is sub C, i.e. a difference image between g2C(x,y) and f2C(x,y) which are outputted from the pixel-shifted image generating unit C53. Determined by a difference image extracting unit D58, based on the following expression (48), is sub D, i.e. a difference image between g2D(x,y) and f2D(x,y) which are outputted from the pixel-shifted image generating unit D54. Namely, $$\text{sub } A(x,y)=g2A(x,y)-f2A(x,y) \quad (45)$$

$$\text{sub } B(x,y)=g2B(x,y)-f2B(x,y) \quad (46)$$

$$\text{sub } C(x,y)=g2C(x,y)-f2C(x,y) \quad (47)$$

$$\text{sub } D(x,y)=g2D(x,y)-f2D(x,y) \quad (48)$$

A maximum/minimum extracting unit 59, by comparing sub A, an output from the difference image extracting unit A55, sub B, an output from the difference image extracting unit B56, sub C, an output from the difference image extracting unit C57, and sub D, an output from the difference image extracting unit D58, determines for each pixel a maximum submax(x,y) shown by the following expression (49) and a minimum submin(x,y) shown by the following expression (50). Namely, $$\text{submax}(x,y)=\max\{\text{sub } A(x,y), \text{sub } B(x,y), \text{sub } C(x,y), \text{sub } D(x,y)\} \quad (49)$$

$$\text{submin}(x,y)=\min\{\text{sub } A(x,y), \text{sub } B(x,y), \text{sub } C(x,y), \text{sub } D(x,y)\} \quad (50)$$

Meanwhile, an allowable value arithmetic unit 60 for calculating an allowable value for variation in a gradation value, in each of the detection image f1 and the comparison image g1, determines a representative value (a maximum value, here) of the gradation value (a value of light and shade) in a local area, and then, as shown in the expression (51) as a function of the representative value as is the case with the expression (17), determines the following allowable value d(x, y) for variation in the gradation value for each pixel.

$$d(x,y)=((\max1+\max2)/2)^*\gamma+\epsilon \quad (51)$$

(where, γ is a real number greater than zero, and ε is an integer greater than zero)

$$\max1=\max\{f1(x,y), f1(x+1,y), f1(x,y+1), f1(x+1,y+1)\} \quad (52)$$

$$\max2=\max\{g1(x,y), g1(x-1,y), g1(x,y-1), g1(x-1,y-1)\} \quad (53)$$

A defect judging circuit 61, adding and subtracting the above-determined allowable value d(x,y) for variation in the gradation value to submax(x,y) and from submin(x,y) determined by the maximum/minimum extracting unit 59, judges a pixel, on which the signs of the both are opposite, to be an non-defective candidate and a pixel, on which the signs of the both are same, to be a defective candidate. Namely, the defect judging circuit 61 judges a pixel at the position(x,y), if the following relation (54) is satisfied, to be an non-defective candidate, and the pixel at the position (x,y), if the following relation (54) is not satisfied, to be a defective candidate. The defect judging circuit 61 outputs, for the non-defective candidate pixel, def(x,y) having a value of, for example, zero, and outputs, for the defective candidate pixel, def(x,y) having a value of, for example, one or more. The expression (54) means that the polarities differ with each other in the relation between {submax(x,y)+d(x,y)} and {submin(x,y)−d(x,y)}.

$$\{\text{submax}(x,y)+d(x,y)\}^*\{\text{submin}(x,y)-d(x,y)\}\leq O \quad (54)$$

Parameters α and β in the present second embodiment have the same meaning as the parameters α and β in the first embodiment do. In the first embodiment, in order to allow an infinitesimal position shift of an individual pattern edge, B(x,y), i.e. the second term in the threshold values thH(x,y) and thL(x,y) shown in the above-mentioned expressions (13) and (14), is adjusted by α and β. Whereas, in the present second embodiment, the position is actually shifted by ±α and ±β between the detection image f1(x,y) and the comparison image g1(x,y). This brings about an effect of allowing the infinitesimal position shift of the pattern edges (the infinitesimal position shift caused by an infinitesimal difference due to the pattern configuration and the distortion in the patterns). The reason is explained below, using FIG. 9 and FIG. 10.

Figure 9:
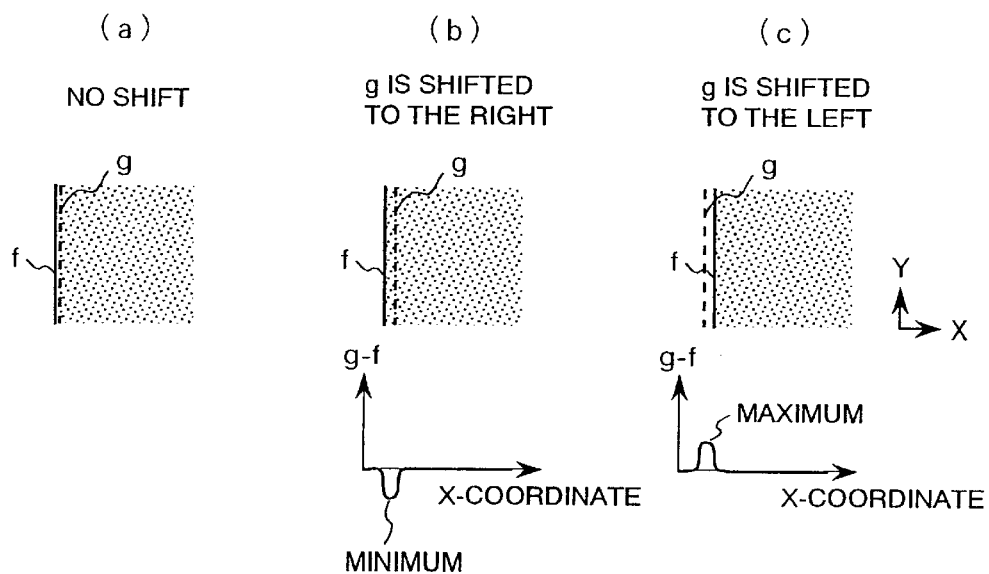
FIGS. 9(a), (b), and (c) are diagrams for explaining a meaning of generation of a position-shifted image in connection with the second embodiment of the present invention.
Figure 10:
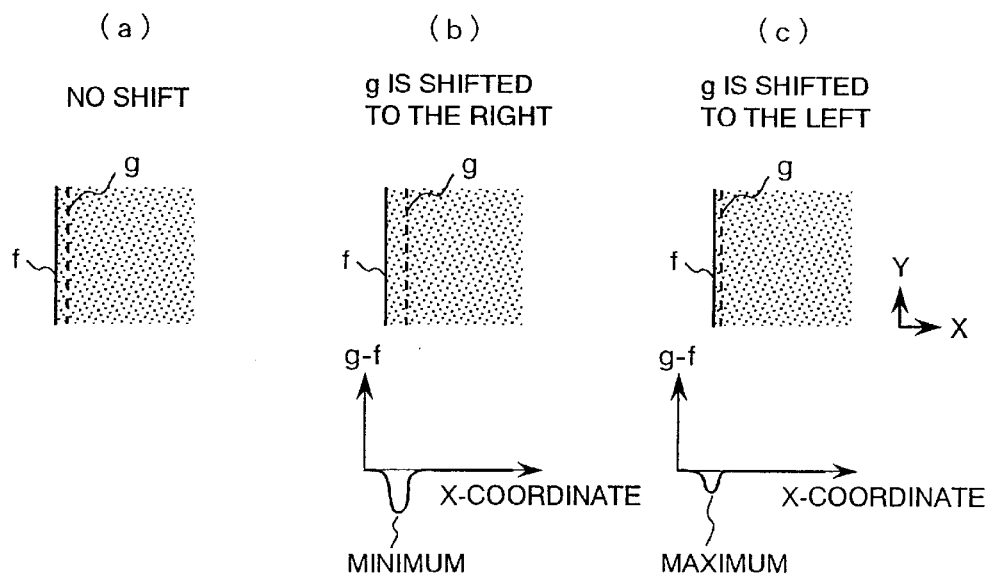
FIGS. 10(a), (b), and (c) are diagrams for explaining a meaning of generation of a position-shifted image, as is the case with the FIGS. 9(a), (b), and (c)

FIG. 9 and FIG. 10 shows the two images to be compared, paying attention to certain specific pattern edges in the two images. An edge of the image f is indicated by a full line and an edge of the image g is indicated by a dotted line. Here, for simplicity, the gradation value of the image f and that of the image g are assumed to be equal to each other, and the position is shifted only in a x-direction.

FIG. 9(*a*) shows a case in which there is no infinitesimal position shift of the pattern edges between the image f and the image g. Then, if the image g is shifted to the right as shown in FIG. 9(*b*), a difference image (g−f) takes a negative value as its minimum (which corresponds to submin(x,y) shown by the expression (50)) at the edge part. On the contrary, if the image g is shifted to the left as shown in FIG. 9(*c*), the difference image (g−f) takes a positive value as its maximum (which corresponds to submax(x,y) shown by the expression (49)) at the edge part. When, from the beginning, there exists no position shift between the image f and the image g, no matter how small the quantity by which the image g is shifted with reference to the image f, polarity (sign) at the minimum or the maximum of the difference image (g−f) at the edge is, at the minimum shown in FIG. 9(b), a negative polarity, and at the maximum shown in FIG. 9(c), a positive polarity.

On the other hand, FIG. 10(a) shows a case in which there exists an infinitesimal position shift of the pattern edges. At this time, if the quantity by which the image g is shifted with reference to the image f is small compared with the above-mentioned infinitesimal position shift, as is shown in FIG. 9(b) and FIG. 9(c), whether the image g is shifted to the right or left, the polarity (sign) at the minimum (which corresponds to submin(x,y) shown by the expression (50)) or the maximum (which corresponds to submax(x,y) shown by the expression (49)) of the difference image (g−f) at the edge is a negative polarity. Generally speaking, when the image g is shifted in both directions, the polarity (sign) at the minimum or the maximum is changed, that is, {submax(x,y)+d(x,y)}*{submin(x,y)−d(x,y)}≦O is satisfied, the pixel is judged to be a non-defective candidate, and the polarities (signs) at the minimum and the maximum are the same, that is, {submax(x,y)+d(x,y)}*{submin(x,y)−d(x,y)}≦O is not satisfied, the pixel is judged to be a defective candidate. In this situation, accordingly, so as not to be judged to be the defective candidate even if there exists the infinitesimal position shift of the pattern edges shown in FIG. 10(a), the shift quantity must be a certain magnitude or more. In other words, the shift quantity makes it possible to adjust to what extent the pattern edges should be allowed. The parameters α and β in the second embodiment correspond to this quantity. Namely, α and β are parameters which are capable of controlling an allowable value for the position shift of the pattern edges.

Also, d(x,y), which is represented by the expression (51) in the present second embodiment, has a function of allowing an infinitesimal difference in the gradation value (the value of light and shade) as is the case with C(x,y) (refer to the expression (17)) in the first embodiment. In the description of the FIG. 9 and FIG. 10, the gradation value of the image f and that of the image g are assumed to be equal to each other. If there is a difference between the gradation values, there occurs an error in sign of the difference image after the shift. Consequently, before comparing the polarities in accordance with the expression (54), d(x,y), i.e. an allowable value for variation in the gradation value, is added {submax(x,y)+d(x,y)} or subtracted {submin(x,y)−d(x,y)} so that the difference between the gradation values exert no influence on the polarity (sign) of the difference image. Although, d(x,y) is set to be a summation of a constant ε and a value obtained by multiplying a representative value of a gradation value in the local area (here, a maximum value) by a proportionality constant γ, as explained in the description of the first embodiment, if the way a gradation value varies is known, a function suitable therefor should be selected.

In the present embodiment, the position shift quantity as the whole small area, which is obtained as the result of the one pixel or less of position shift detection, is utilized as the origin coordinate at the time of generating the position-shifted images. The infinitesimal position shift of the individual pattern edge is allowed by generating the images the position of which are shifted in a variety of directions. Moreover, the infinitesimal difference in gradation value is allowed by calculating the allowable value for variation in the gradation value for each local area. Also, as is the case with the first embodiment, the parameters α, β, γ and ε make it possible to freely control the position shift and the allowable quantity for variation in the gradation value Modifications of the Second Embodiment In the present second embodiment, too, as is the case with the first embodiment, when the detecting unit 101 detects an image with a high position accuracy and a position error of the detected image is less than one pixel, it is possible to omit the pixel unit of position alignment.

Also, when the detecting unit 101 detects an image with an even higher position accuracy and the position error of the detected image is substantially negligible, it is possible to omit both the pixel unit of position alignment and the one pixel or less of position shift detection.

Also, although the linear interpolation in the expressions (37) to (44) is employed, there can be a modification in which a more precise bilinear interpolation is employed. In this case, the expressions (37) to (44) are replaced by the following expressions (55) to (62).

$$f2A(x,y)=f1(x+\delta x0+\alpha,y+\delta y0)=(1-\delta x0-\alpha)(1-\delta y0)\,f1(x,y)+(\delta x0+\alpha)(1-\delta y0)f1(x+1,y)+(1-\delta x0-\alpha)\delta y0f1(x,y+1)+(\delta x0+\alpha)\delta y0f1(x+1,y+1) \quad (55)$$

$$g2A(x,y)=g1(x-\delta x0-\alpha,y-\delta y0)=(1-\delta x0-\alpha)(1-\delta y0)\,g1(x,y)+(\delta x0+\alpha)(1-\delta y0)g1(x-1,y)+(1-\delta x0-\alpha)\delta y0g1(x,y-1)+(\delta x0+\alpha)\delta y0g1(x-1,y-1) \quad (56)$$

$$f2B(x,y)=f1(x+\delta x0-\alpha,y+\delta y0)=(1-\delta x0+\alpha)(1-\delta y0)f1(x,y)+(\delta x0-\alpha)(1-\delta y0)f1(x+1,y)+(1-\delta x0+\alpha)\delta y0f1(x,y+1)+(\delta x0-\alpha)\delta y0f1(x+1,y+1) \quad (57)$$

$$g2B(x,y)=g1(x-\delta x0+\alpha,y-\delta y0)=(1-\delta x0+\alpha)(1-\delta y0)\,g1(x,y)+(\delta x0-\alpha)(1-\delta y0)g1(x-1,y)+(1-\delta y0+\alpha)\delta y0g1(x,y-1)+(\delta x0-\alpha)\delta y0g1(x-1,y-1) \quad (58)$$

$$f2C(x,y)=f1(x+\delta x0,y+\delta y0+\beta)=(1-\delta x0)(1-\delta y0-\beta)f1(x,y)+\delta x0(1-\delta y0-\beta)f1(x+1,y)+(1-\delta x0)(\delta y0+\beta)f1(x,y+1)+\delta x0(\delta y0+\beta)f1(x+1,y+1) \quad (59)$$

$$g2C(x,y)=g1(x-\delta x0,y-\delta y0-\beta)=(1-\delta x0)(1-\delta y0-\beta)g1(x,y)+\delta x0(1-\delta y0-\beta)g1(x-1,y)+(1-\delta x0)(\delta y0+\beta)g1(x,y-1)+\delta x0(\delta y0+\beta)g1(x-1,y-1) \quad (60)$$

$$f2D(x,y)=f1(x+\delta x0,y+\delta y0-\beta)=(1-\delta x0)(1-\delta y0+\beta)f1(x,y)+\delta x0(1-\delta y0+\beta)f1(x+1,y)+(1-\delta x0)(\delta y0-\beta)f1(x,y+1)+\delta x0(\delta y0-\beta)f1(x+1,y+1) \quad (61)$$

$$g2D(x,y)=g1(x-\delta x0,y-\delta y0+\beta)=(1-\delta x0)(1-\delta y0+\beta)g1(x,y)+\delta x0(1-\delta y0+\beta)\,g1(x-1,y)+(1-\delta x0)(\delta y0-\beta)g1(x,y-1)+\delta x0(\delta y0-\beta)g1(x-1,y-1) \quad (62)$$

Also, concerning directions in which an image is shifted, there can be a modification in which, adding oblique directions, eight directions are employed instead of the above-described four, i.e. up-and-down and right-to-left, directions. The shift with eight directions brings about an advantage of making the allowed shift quantity more isotropic than the shift with four directions. In this case, it becomes necessary to provide eight of position-shifted image generating units and difference extracting units, respectively, whereas necessary in FIG. 8 are four of the position-shifted image generating units 51 to 54 and the difference extracting units 55 to 58, respectively. A magnitude of a shift quantity with the oblique directions should be equal to that of a shift quantity with the up-and-down and right-to-left directions, and thus the expressions should be replaced by the following expressions (63) to (70).

$$f2E(x,y)=f1(x+\delta x0+\alpha/\sqrt{2},\ y+\delta y0+\beta/\sqrt{2}) \quad (63)$$

$$g2E(x,y)=g1(x-\delta x0-\alpha/\sqrt{2},\ y-\delta y0-\beta/\sqrt{2}) \quad (64)$$

$$f2F(x,y)=f1(x+\delta x0+\alpha/\sqrt{2},\ y+\delta y0-\beta/\sqrt{2}) \quad (65)$$

$$g2F(x,y)=g1(x-\delta x0-\alpha/\sqrt{2},\ y-\delta y0+\beta/\sqrt{2}) \quad (66)$$

$$f2G(x,y)=f1(x+\delta x0-\alpha/\sqrt{2},\ y+\delta y0+\beta/\sqrt{2}) \quad (67)$$

$$g2G(x,y)=g1(x-\delta x0+\alpha/\sqrt{2},\ y-\delta y0-\beta/\sqrt{2}) \quad (68)$$

$$f2H(x,y)=f1(x+\delta x0-\alpha/\sqrt{2},\ y+\delta y0-\beta/\sqrt{2}) \quad (69)$$

$$g2H(x,y)=g1(x-\delta x0+\alpha/\sqrt{2},\ y-\delta y0+\beta/\sqrt{2}) \quad (70)$$

Regarding a method of interpolation in the oblique directions, too, possible are a linear interpolation, a bilinear interpolation, and so on. Also, there can be a modification in which, as is the case with the fourth modification of the first embodiment, the following expressions (71) to (73) are employed instead of the expression (51).

$$d(x,y)=((ave1+ave2)/2)*\gamma+\epsilon \quad (71)$$

where $$ave1=\{f1(x,y)+f1(x+1,y)+f1(x,y+1)+f1(x+1,y+1)\}/4 \quad (72)$$

$$ave2=\{g1(x,y)+g1(x-1,y)+g1(x,y-1)+g1(x-1,y-1)\}/4 \quad (73)$$

Otherwise, there can be a modification in which, instead of the expression (51), the sub CPU 45 prepares in advance a look-up table for a representative gradation value of quantities such as maxl (refer to the expression (52)), max2 (refer to the expression (53)), ave1 (refer to the expression (72)), and ave2 (refer to the expression (73), and then the allowable value arithmetic unit 60 determines d(x,y) in accordance with the look-up table.

Modifications common to First Embodiment and Second Embodiment

A method of comparing two images derived from an identical object is shown in the above-described first and second embodiments. It is evident, however, that the content in the image processing unit can be embodied in much the same way even when comparing with an image obtained by detecting anther object and storing it in advance or with an image generated from design data.

Also, a case of apparatuses employing an electronic optical detecting means is described in the above-described first and second embodiments. It is needless to say, however, that the content in the present invention can be embodied in much the same way even when employing any kind of detecting means such as the optical detecting means shown in FIG. 4.

Figure 4:
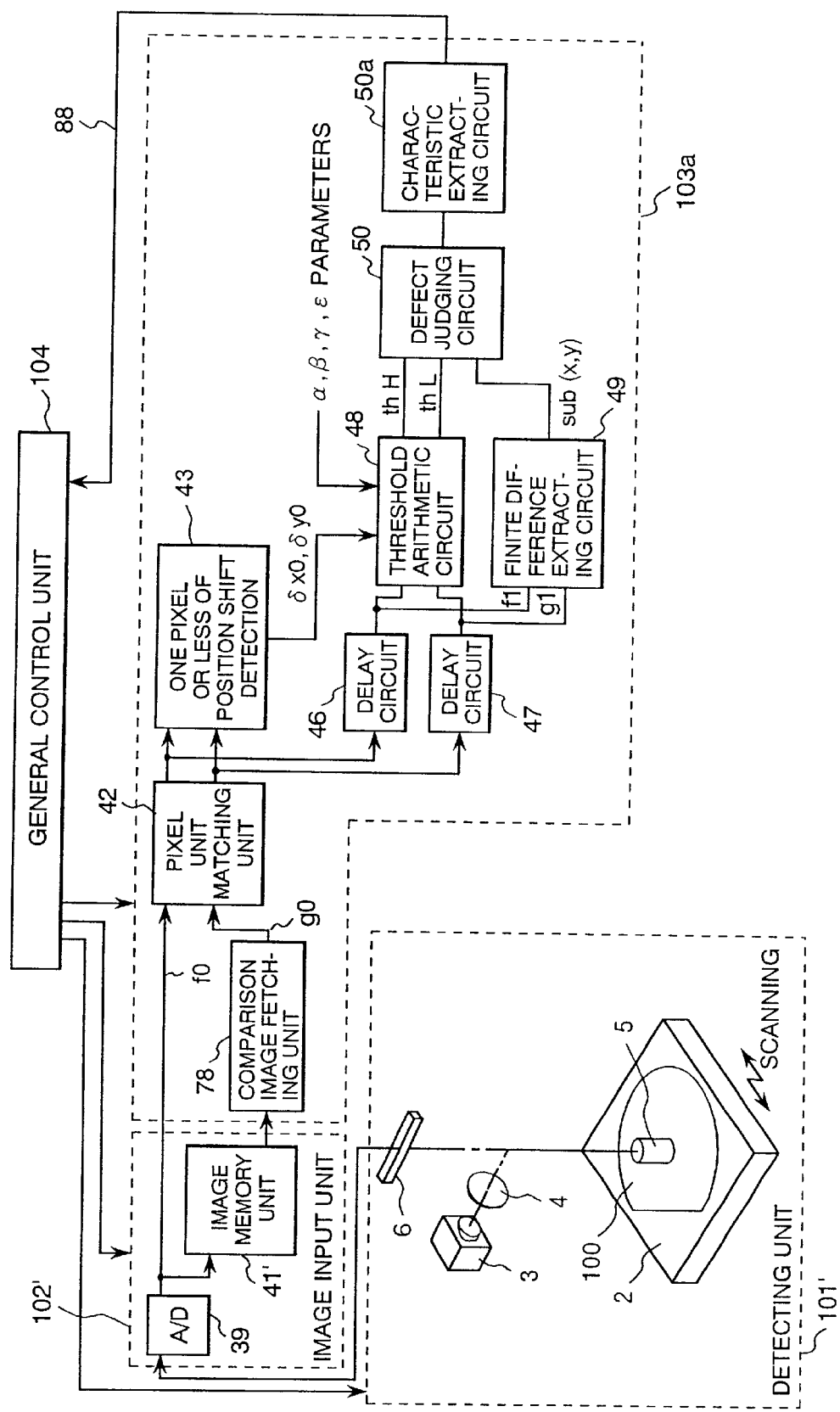
FIG. 4 is a schematic configuration diagram showing a first embodiment of a method of inspecting a pattern and an apparatus thereof in which an optical microscope in connection with the present invention is employed.

Namely, FIG. 4 shows a brief configuration of an apparatus of inspecting a pattern in which an optical detecting means (a detecting unit) 101' is employed. The detecting unit 101' comprises a stage 2 for mounting an object to be inspected 100 such as a semiconductor wafer and moving it in a x-direction and a y-direction, an light source 3, an illuminating optical system 4 for gathering a light beam emitted from the light source 3, an objective lens 5 for illuminating an illuminating light beam gathered by the illuminating optical system 4 to the object to be inspected 100 and focusing an optical image reflected from the object to be inspected 100, and a one-dimensional image sensor 6, i.e. an embodiment of a photoelectric converter for receiving an optical image focused by a detecting optical system including the objective lens 5 and converting it into an image signal corresponding to the illumination. The image signal detected by the one-dimensional image sensor 6 in the detecting unit 101' is inputted into an image inputting unit 102'. The image inputting unit 102 has an A/D converter 39 and an image memory unit 41' for storing a digital image signal, which has a gradation value(a value of light and shade) obtained from the A/D converter 39, so as to create a comparison image g 0 from the digital image signal. Naturally, it is allowable that the image inputting unit 102' is provided with a preprocessing circuit 40 for a shading amendment, a dark level amendment, a filtering process, and so on. An image processing unit 103*a*, the configuration of which is the same as the configuration shown in FIG. 1, is able to perform a judgement, based on the same image processing, as to whether a defective candidate or a non-defective candidate, and a calculation of a characteristic quantity about the defective candidate. The image processing unit 103*a*, however, is provided with a comparison image fetching unit 78 for fetching the comparison image from the image memory unit 41'. In this way, the delay circuit 41 shown in FIG. 1 may be replaced by the image memory 41' and the comparison image fetching unit 78.

The present invention exhibits an effect of making it possible to decrease the number of false information, which is caused by mismatches such as an infinitesimal difference in pattern configuration, a difference in gradation value, distortion of a pattern, and a position shift attributed to an object to be inspected and an image detecting system, and to detect a more microscopic defect or a candidate for a more microscopic defect.

The present invention also exhibits an effect of, when a pattern formed on an object to be inspected is inspected by means of an electron microscope, making it possible to decrease the number of false information, which is caused by mismatches such as an infinitesimal difference in pattern configuration, a difference in gradation value, distortion of the pattern, and a position shift attributed to the object to be inspected and an image detecting system, and to detect a more microscopic defect or a candidate for a more microscopic defect.

The present invention also exhibits an effect of making it possible to obtain an image signal having a stable gradation value (a value of light and shade) from an inspection through an electron microscope of a pattern formed on an object to be inspected, and thus to stably detect a more microscopic defect or a candidate for a more microscopic defect.

What is claimed is:

1. A method for inspecting a pattern, comprising the steps of:

acquiring a first image of a first area on a sample by imaging said first area formed as a first pattern;

memorizing said first image;

acquiring a second image of a second area on said sample by imaging said second area formed as a second pattern which is to be the same as said first pattern; and detecting a defect of said first pattern by acquiring a differential image between said first image and said second image;

wherein, in the step of detecting said defect, said differential image is processed by using information of brightness corresponding to both of said first image and said second image.

2. The method for inspecting a pattern as claimed in claim 1, wherein said information is used for setting a threshold value for processing said differential image.

3. The method for inspecting a pattern as claimed in claim 1, wherein said differential image is processed by using information concerning brightness of pixels of said first image and said second image and information concerning brightness of pixels in the vicinity of said first image and said second image for detecting said defect.

4. The method for inspecting a pattern as claimed in claim 1, wherein said first image and said second image are electron images acquired by detecting a secondary electron or a reflected electron which is radiated from said sample by irradiating an electron beam on said sample.

5. The method for inspecting a pattern as claimed in claim 4, wherein a dispersion in brightness of said electron images is previously acquired, said differential image is processed by using information of brightness corresponding to pixels of said first image and said second image and information concerning brightness of pixels in the vicinity of said first image and said second image and information of said dispersion in brightness.

6. A method for inspecting a pattern, comprising the steps of:
    acquiring a first image of a first area on a sample by imaging said first area formed as a first pattern;
    memorizing said first image;
    acquiring a second image of a second area on said sample by imaging said second area formed as a second pattern which is to be the same as said first pattern;
    compensating said memorized first image and said second image;
    detecting a defect of said first pattern by acquiring a differential image between said first image and said second image;
    wherein, in the step of detecting said defect, said differential image is processed by using threshold values set at each small area of said first and second images for detecting said defect.

7. A method for inspecting a pattern as claimed in claim 6, wherein said first image and said second image are divided into said small areas, and said threshold values are determined depending on brightness of said small areas.

8. A method for inspecting a pattern as claimed in claim 6, wherein the step of said compensating compensates for a position shift between said first image and said second image and a dispersion in brightness between said first image and said second image.

9. A method for inspecting a pattern as claimed in claim 6, wherein said threshold values are set at each small area depending on the brightness of each small area.

10. A method for inspecting a pattern as claimed in claim 6, wherein the step of compensating compensates for a position shift between said first image and said second image pixel by pixel.

11. A method for inspecting a pattern, comprising the steps of:
    acquiring a first electron image by detecting a secondary electron or a reflected electron which is radiated from a first area formed as a first pattern on a sample by irradiating an electron beam on said first area;
    memorizing said first electron image;
    acquiring a second electron image by detecting a secondary electron or a reflected electron which is radiated from a second area formed as a second pattern which is to be the same as said first pattern by irradiating said electron beam on said second area;
    compensating for at least shading concerning said first electron image and said second electron image;
    acquiring a differential image between said first electron image compensated in shading and said second image compensated in shading; and
    processing said differential image by using information of brightness of said first electron image and said second electron image for detecting a defect.

12. A method for inspecting a pattern as claimed in claim 11, wherein said information is used for setting a threshold value for processing said differential image.

13. A method for inspecting a pattern as claimed in claim 11, wherein said differential image is processed by using information of brightness of pixels in the vicinity of pixels of said first electron image and said second electron image in addition to said information for detecting said defect.

14. A method for inspecting a pattern as claimed in claim 11, wherein a dispersion in brightness of said electron images is previously acquired, said differential image is processed by using information relating to said dispersion in brightness in addition to said information for detecting said defect.

15. An apparatus for inspecting a pattern, comprising:
    an image acquiring unit which acquires an image from a sample formed with a pattern by imaging said sample;
    a memory which memorizes said image acquired by said image acquiring unit; and
    a defect detecting device which detects a defect of a pattern by acquiring a differential image between a first image and a second image, said first image being acquired from said pattern formed on a first area of said sample by said image acquiring unit and memorized in said memory, and said second image being acquired from a second area of said sample formed with a pattern which is to be the same as said pattern on said first area;
    wherein said defect detecting device processes said differential image using information of each brightness concerning said first image and said second image.

16. An apparatus for inspecting a pattern as claimed in claim 15, wherein said information is used for setting a threshold value for processing said differential image.

17. An apparatus for inspecting a pattern as claimed in claim 15, wherein said information includes information of brightness of pixels corresponding to said first image and said second image and information of brightness of pixels in the vicinity of pixels of said first image and said second image.

18. An apparatus for inspecting a pattern, comprising:
    an electron irradiating unit which irradiates an electron to a sample formed with a pattern;
    an electron image acquiring unit which acquires an electron image of said sample by detecting a secondary electron or a reflected electron from said sample to which said electron is irradiated by said electron irradiating unit;
    a memory which memorizes a first electron image acquired from a first area of said sample by said electron image acquiring unit;
    an image compensation unit which compensates for shading of an image concerning said first electron image and a second electron image acquired from a second area of said sample by said electron image acquiring unit;
    a differential image calculating unit which calculates a differential image between said first electron image and said second electron image; and
    a defect detecting unit which processes said differential image by using information of brightness of said first electron image and said second election image.

19. An apparatus for inspecting a pattern as claimed in claim 18, wherein said information is used for setting a threshold value for processing said differential image.

20. An apparatus for inspecting a pattern as claimed in claim 18, wherein said defect detecting unit processes said differential image by using information of brightness of pixels in the vicinity of pixels of said first electron image and said second electron image in addition to said information.

21. An apparatus for inspecting a pattern as claimed in claim 18, wherein said defect detecting unit processes said differential image by using a dispersion in brightness between said first electron image and said second electron image calculated beforehand in addition to said information.

22. An apparatus for inspecting a pattern as claimed in claim 18, wherein said image compensation unit compensates for a position shift between said first electron image and said second electron image.

23. An apparatus for inspecting a pattern as claimed in claim 18, wherein said image compensation unit compensates for a position shift pixel by pixel between said first electron image and said second electron image.

* * * * *